(12) United States Patent
Bainbridge et al.

(10) Patent No.: US 8,577,719 B2
(45) Date of Patent: Nov. 5, 2013

(54) STRATEGIC QUALITY SUPPORT SYSTEM

(76) Inventors: Darlene Danece Bainbridge, Cuba, NY (US); Nicole Christina Travis, Cuba, NY (US)

(*) Notice: Subject to any disclaimer, the term of this patent is extended or adjusted under 35 U.S.C. 154(b) by 0 days.

(21) Appl. No.: 13/349,620

(22) Filed: Jan. 13, 2012

(65) Prior Publication Data

US 2013/0185108 A1    Jul. 18, 2013

(51) Int. Cl.
  *G06Q 10/00*    (2012.01)
  *G06Q 40/00*    (2012.01)
(52) U.S. Cl.
  USPC ....... 705/7.42; 705/7.11; 705/7.12; 705/7.13; 705/7.15; 705/7.24; 705/7.27; 705/7.28; 705/7.36; 705/7.38; 705/7.39; 705/7.41
(58) Field of Classification Search
  USPC ......................................................... 705/7.15
  See application file for complete search history.

(56) References Cited

U.S. PATENT DOCUMENTS

| | | | | |
|---|---|---|---|---|
| 7,324,878 | B2* | 1/2008 | Imai et al. .......................... | 701/1 |
| 2002/0029161 | A1* | 3/2002 | Brodersen et al. ................ | 705/9 |
| 2002/0120642 | A1* | 8/2002 | Fetherston .................... | 707/500 |
| 2003/0045958 | A1* | 3/2003 | Brandt et al. ................. | 700/101 |
| 2003/0055669 | A1* | 3/2003 | Ryan et al. .......................... | 705/1 |
| 2003/0069983 | A1* | 4/2003 | Mukund ........................ | 709/229 |
| 2003/0149598 | A1 | 8/2003 | Santoso et al. | |
| 2004/0117233 | A1* | 6/2004 | Rapp, III .......................... | 705/9 |
| 2005/0108050 | A1 | 5/2005 | Knapheide | |
| 2005/0273216 | A1* | 12/2005 | Imai et al. .......................... | 701/1 |
| 2006/0053035 | A1* | 3/2006 | Eisenberg ........................ | 705/2 |
| 2006/0167989 | A1* | 7/2006 | Bashen et al. ................ | 709/203 |
| 2006/0282302 | A1 | 12/2006 | Hussain | |
| 2007/0129983 | A1 | 6/2007 | Scherpbier et al. | |
| 2007/0260503 | A1* | 11/2007 | Pan et al. .......................... | 705/9 |
| 2007/0260506 | A1* | 11/2007 | Fitzpatrick et al. ............. | 705/11 |
| 2008/0164998 | A1 | 7/2008 | Scherpbier et al. | |
| 2009/0043634 | A1 | 2/2009 | Tisdale | |
| 2009/0313046 | A1 | 12/2009 | Badgett et al. | |
| 2010/0088119 | A1 | 4/2010 | Tipirneni | |

(Continued)

FOREIGN PATENT DOCUMENTS

| | | | |
|---|---|---|---|
| WO | WO 2005/038691 A2 | 4/2005 | |
| WO | WO 2006/116529 A2 | 11/2006 | |

OTHER PUBLICATIONS

Seddon et al. Task Manager: an innovative approach to improving hospital communication after hours. The New Zealand Medical Journal. Oct 15, 2010. pp. 57-66. vol. 123 No. 1324, The New Zealand Medical Association, New Zealand.

*Primary Examiner* — Leland Marcus
(74) *Attorney, Agent, or Firm* — Patent Technologies, LLC; Robert D. Gunderman, Jr.

(57) ABSTRACT

Healthcare providers are faced with an extremely fast paced environment where patient care is closely coupled with quality and safety standards. To promote a safe and optimal environment for patients and healthcare workers, numerous standards must be met. The number of standards continues to grow as healthcare continues to become more complex.

The present invention, and the various embodiments thereof, describes a computer based system and method for strengthening a healthcare provider's quality program through the use of quality assurance, quality improvement and performance improvement modules that help to structure, monitor and manage quality tasks. A pixel mapped calendar provides a compelling graphical representation of the current status of the various quality tasks associated with a specific date or dates to provide a visual representation of the overall health of an organization as it relates to meeting quality and safety standards.

21 Claims, 35 Drawing Sheets

(56) References Cited

U.S. PATENT DOCUMENTS

| | | |
|---|---|---|
| 2010/0169119 A1 | 7/2010 | Hussain |
| 2011/0125539 A1 | 5/2011 | Bollapragada et al. |
| 2011/0218815 A1* | 9/2011 | Reiner .............................. 705/2 |

* cited by examiner

STRATEGIC Quality SUPPORT SYSTEM

Logged in as Mary Smith, logout

My QCs Scheduled Tasks QA calendar Validations QC calendar PT calendar Reviews Providers Absences -- Show Future Events --

You have 2 Just Do Its.

My QCs

Business Office

| Name | Links | Due | Notes | | |
|---|---|---|---|---|---|
| Testing Water Quality | | Nov 15 3:00 PM | Primary | | ✕ |

Lab

| Name | Links | Due | Notes | | |
|---|---|---|---|---|---|
| Temp Check | | Nov 15 5:00 PM | Primary | ⚠ | ✕ |
| Blood Bank Temperature | | Nov 15 6:00 PM | Primary | ⚠ | ✕ |

STRATEGIC Quality SUPPORT SYSTEM

← Show Future Events →

Listing Future Events
Primary Events

| Name | Due |
|---|---|
| Temp Check | Jul 14 4:00 PM |
| Daily Refrigerator Temperature Checks | Jul 14 12:00 PM |
| Temp Check | Jul 15 4:00 PM |
| Daily Refrigerator Temperature Checks | Jul 15 12:00 PM |

Backup Events

Validator Events

Fig. 10

Name: Obstetrics (Edit)

Provider: Sample Hospital

Managers:
Mary Smith

New Quality Initiative
Quality Initiatives

Task Groups

Add Task Group

Members

Create User

-- Select One --    Add User

STRATEGIC QUALITY SUPPORT SYSTEM

BACKGROUND OF THE INVENTION

1. Field of the Invention

This invention relates generally to information technology systems, and more particularly to a computer based system and method for strengthening a healthcare provider's quality program.

2. Description of Related Art

Healthcare has transformed over the past thirty years into a technologically advancing, safety critical industry with a declining sphere of influence over its own future because of a reputation for unstable quality. Many of health care's current struggles result from an environment where technology has repeatedly transformed the dynamics of patient care delivery while its efforts to control the new risks natural to that evolution have failed to keep pace. At the same time that technology has allowed health care to advance what it can do to improve the quality and longevity of life, it has introduced an environment where it is easier for preventable harm to touch the life of a patient. The design and operations of a provider's approaches to quality management, particularly safety management, play critical roles in just how well all the industry's technologies work to advance the success of its providers and service the public. Whether the industry's quality approaches can effectively manage the natural tension between innovation and safety determines the end-product of health care.

Managing quality in a fast paced environment where the demands on the workforce increase as a natural by-product of technological growth can be a challenge. The approach to quality in these environments is particularly important as its primary purpose is to maintain the reliability of a product or service in delivering on desired outcomes as the variables that challenge the ability to achieve those outcomes grow in number and complexity. It has become important to overcome the problems created by health care's current retrospective, reactive, and bureaucratic approaches that are costing the industry too much in terms of patient lives, money, resources, morale and the support of its public.

In its simplest form, quality is defined as how well a business does what it does. For health care's public, this is measured in patient perception of a provider's ability to deliver patient care in ways that offer optimal outcomes given the knowledge, science and evidence currently available. Much of that is measured in how well providers manage the patient care environment to promote optimal safety and deliver care consistent with currently known standards while keeping care patient-focused. The majority of the measures that feed patient perception fall into the categories of reliability, resilience, the skill to deliver care consistent with current evidence-based standards untouched by error and the ability to meet individualized patient needs. It is health care's ability to make patients feel well cared for and personally cared about.

Health care is estimated to have approximately 3000 standards that must currently be managed in order to promote safe and optimal environments for patients and workers. That number is growing every day as new science and experience introduce new knowledge while the dynamics of a technologically advancing environment continuously introduces new risks and shifts existing risks. The average hospital department has between 75 and 145 basic standards that translate into several hundreds of tasks that need to be managed in addition to the patient care and operational support activities that are also growing in number. For a typical one hundred bed hospital, this translates into the need to manage approximately 10,000 safety related activities annually in addition to the growing number of evidence-based standards that define clinically appropriate patient care and service-oriented activities directed at patient satisfaction. How all of these standards come together determines the odds of how great an experience a patient can have. In spite of millions (and probably billions) of dollars and too many man-hours to count, health care is struggling to keep pace with its own environment because it can't effectively manage all of these standards. Much of that struggle exists because its approaches to quality are too slow, too resource-intensive and deliver too little too late.

It is therefore an object of the present invention to provide a system and method for strengthening a quality program of a healthcare provider. It is another object of the present invention to provide a system and method for managing quality initiatives for timely and effective improvement. It is another object of the present invention to provide a system and method for strengthening reliability, resilience, and workforce performance potential while reducing the costs associated with errors. It is yet another object of the present invention to provide a system and method for providing and updating a quality assurance monitoring tool that resembles a calendar having a pixel mapped format that allows for real time monitoring and action in a way that reduces the risk of an error making it all the way to a patient. These and other objects of the present invention will become evident to one skilled in the art after a review of this specification, claims, and the attached drawings.

BRIEF SUMMARY OF THE INVENTION

In accordance with the present invention, there is provided a computer-based Strategic Quality Support System for strengthening a healthcare provider's quality program comprising a computer having a processor, memory, and access to computer readable media; a computer program stored on computer readable media having a quality assurance module, a quality improvement module, and a performance improvement module; a user interface displayed on a computer monitor for interaction with said computer program; a network connection between the computer and a computer network for allowing remote access to the computer program; a pixel mapped calendar stored on computer readable media and graphically displayed on a computer monitor having a plurality of status indicators for each date, each status indicator being a pixel and being assigned a color corresponding to a current status of a quality assurance task; a task overview function stored on computer readable media and displayed on a computer monitor containing a visual representation of task compliance for each quality assurance task using a plurality of colored geometries where each color has significance, and a task compliance output stored on computer readable media and displayed on a computer monitor where quality assurance compliance percentages are depicted for a specified historical period.

The foregoing paragraph has been provided by way of introduction, and is not intended to limit the scope of this invention as defined by this specification, claims, and the attached drawings.

BRIEF DESCRIPTION OF THE DRAWINGS

The invention will be described by reference to the following drawings, in which like numerals refer to like elements, and in which:

FIG. 6 is a screenshot depicting the My QCs screen;

FIG. 7 is a screenshot depicting compliant data entry in the My QCs screen;

FIG. 8 is a screenshot depicting non-compliant data entry in the My QCs screen;

FIG. 9 is a screenshot depicting not applicable data entry in the My QCs screen;

FIG. 10 is a screenshot depicting listing of events;

FIG. 12 is a screenshot depicting adding a task group;

FIG. 14 is a screenshot depicting a Just-Do-It Reporting screen;

FIG. 17 is a screenshot depicting a Just-Do-It severity prioritization screen;

FIG. 24 is a screenshot depicting a create absence screen;

FIG. 30 is a screenshot depicting new performance improvement initiative entry;

FIG. 31 is a screenshot depicting quality and performance improvement initiatives;

Figure 1:
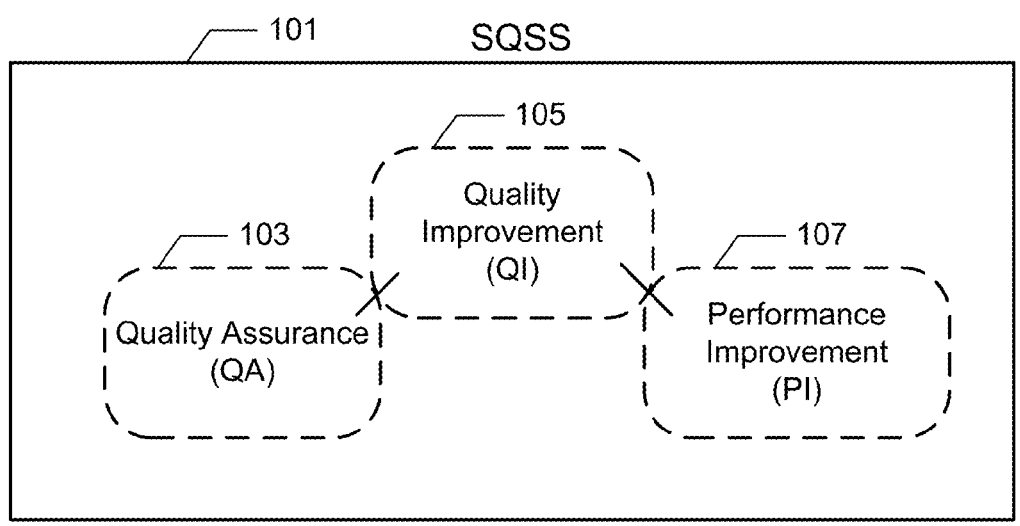
FIG. 1 is a diagram depicting major modules of the Strategic Quality Support System.

The present invention will be described in connection with a preferred embodiment; however, it will be understood that there is no intent to limit the invention to the embodiment described. On the contrary, the intent is to cover all alternatives, modifications, and equivalents as may be included within the spirit and scope of the invention as defined by this specification, claims, and the attached drawings.

DESCRIPTION OF THE PREFERRED EMBODIMENTS

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

Strategic Quality Support System (SQSS) is a computer based system to assist healthcare providers in making that next strategic move to strengthen their quality programs for the current healthcare market. In some embodiments of the present invention, the System is network or internet based.

This specification and attached drawings reflect quality management in an exemplary hospital setting, but the present invention is applicable to any health care setting or industries where managing a range of variables to ensure the safety and quality of the final product or service is important.

Rather than studying activities after the fact to see if caregivers got it right. SQSS supports the workforce in managing activities up front to know they are getting them right. Instead of working with small sample sizes and hoping that there are no hidden surprises in unknown numbers, SQSS allows providers to manage quality in simple ways that frequently work at a level of 100% sampling. Instead of finding out that something didn't happen as it was supposed to after it is too late to make it right. SQSS makes the knowledge of non-compliance real time.

One of the important goals of SQSS is to help health care providers more easily achieve five critical business outcomes important to health care's success in today's market. These business outcomes are 1.) patient satisfaction that can lead to patient loyalty, 2.) new patient acquisition, 3.) patient retention, 4.) profitability and 5.) market domination. Each of these outcomes are significantly impacted by the way activities come together in a hypercomplex, fast-paced environment to create the kind of quality in the patient experience that will keep people coming back and telling favorable stories. In order to optimize that impact, SQSS helps providers strengthen three critical variables that influence the patient's experience. These three variables are reliability, resilience, and workforce performance potential. These aspects of operations and care delivery are important as they directly impact a patient's chances of an optimal outcome in a fast paced environment where the number of variables that must be managed for a successful outcome can easily exceed the human capacity of the most diligent caregivers when left to manually ensure they all happen.

In its simplest form, quality is defined as how well a business does what it does. For health care's public, this is measured in patient perception of a provider's ability to deliver patient care in ways that offer optimal outcomes given the knowledge, science and evidence currently available. Much of that is measured in how well providers manage the patient care environment to promote optimal safety and deliver care consistent with currently known standards while keeping care patient-focused. The majority of the measures that feed patient perception fall into the categories of reliability, resilience, the skill to deliver care consistent with current evidence-based standards untouched by error and the ability to meet individualized patient needs. It is health care's ability to make patients feel well cared for and personally cared about.

For a general understanding of the present invention, reference is made to the drawings. In the drawings, like reference numerals have been used throughout to designate identical elements.

FIG. 1 is a diagram depicting major modules of the Strategic Quality Support System 101. Major modules, each of which will be described in detail herein, include a Quality Assurance (QA) module 103, a Quality Improvement (QI)

module 105, and a Performance Improvement (PI) module 107. Quality assurance activities manage day-to-day activities that ensure the safety and quality of patient care as it is delivered. Quality improvement ensures that patient care activities keep pace as science, new knowledge and new evidence advance what health care can offer the public. Performance improvement creates the coordination necessary to move critical masses of people and processes to higher levels of performance in a hypercomplex environment with tight coupling.

One of the most important design features of SQSS is the ability to increase the reliability of the healthcare environment. Reliability is the ability to deliver the same outcome regardless of the variables that may get in its way or shift in the process of delivering patient care. This is achieved in SQSS through the systematization of thousands of quality control activities that must be effectively carried out day in and day out in order to secure an environment that sets the stage to manage the patient experience. Reliability is not the same as repeatability which focuses on the repetition of a specific task or group of tasks. While the repeatability of some basic tasks may be important to achieving reliability, reliability focuses on the delivery of a consistent outcome. For fast paced environments, reliability generally lives in the standardization of certain basic activities related to the safety of the environment and systematization of all other activities so they play up from the basics to ensure outcomes that meet patient specific needs. For example, standardized systematization of crash cart checks is important to ensuring that all the equipment and drugs are readily available in the event of a patient crisis. Utilization of the decision-tree in the ventricular fibrillation algorithm to make the best choices for a patient based on the presentation of symptoms and response to each intervention is an example of the flexible systematization necessary in a dynamic environment where the goal is to practice up from the basics to meet patient specific needs.

The Quality Assurance module of SQSS is designed to increase the consistency of the fixed standards that serve as the jumping off point for creating a reliable patient experience. In the above example, care could be delayed thus reducing the odds of an optimal outcome if all the necessary equipment and medications are not readily available, medications are outdated, equipment is not in working order or caregivers do not carry out critical clinical interventions in the correct order or dosage as appropriate to the patient's clinical response. Reliability of fixed and clinical standards has become a growing problem for health care as its traditional approaches to quality have relied on people to simply remember to make a growing number of environmental and patient care standards happen. While health care's current quality model worked in the early 1980s when what the industry could offer and the pace, demands and risks for industry were much less, it is actually more of a hindrance than a help in the present environment as demands exceed the capacity of the human mind to simply remember to make the thousands of things that need to happen just occur.

Today's health care environment makes it much easier for simple slips to result in less than optimal odds for patients. It is not a factor of how hard caregivers are working or how much they care. It is a factor of an environment that makes it easy for people to fail as the limited capacity of working memory is overloaded and the environmental lack of tools and approaches to improve their odds of success forces people to perform at a less than optimal level. Compliance with the multitude of standards that define an optimally safe patient care environment in today's market is directly related to the degree of stresses and pressures that impact an individual's ability to remember everything that needs to be done at any given moment in time. This set of circumstances puts health care at great risk of deja vous errors and quality drift. The associated risks are compounded by health care's current financial crisis and the fact that most providers have exhausted the discretionary resources that they have historically used to monitor these situations.

The basic premise of the Quality Assurance module 103 in the Strategic Quality Support System is that a provider programs the System with environmental and clinical standards that can easily be organized in a computer-based system and lets the System manage them by working directly with the frontline workers to remind them when they need to occur and keep the documentation to support their occurrence. The System is set to know what needs to be done, when it needs to be done, who is the primary person responsible and who will act as back-up for that individual when they are unavailable. It then simply generates to-do lists every day for all members of the health care team. If everyone takes care of the few tasks on their lists, the organization can ensure the consistency of the patient care environment which is the first important step in achieving reliability. The goal is to free up the mental capacity and time of the workforce so that caregivers can dedicate more time and attention to those things that benefit from the insight and clinical knowledge of a healthcare professional. By bringing together the capabilities of a computer system to manage large quantities of information that can easily be systematized without tiring the skills and knowledge of our healthcare professionals, SQSS assists in strengthening the stability of the patient care environment so the deja vous errors and quality drift are substantially reduced. By ensuring the consistency of the patient care environment, it becomes easier for the workforce to practice up from the basics to meet the individualized needs of the patient which, in turn, fosters the reliability of the patient outcomes.

The degree of green reflected in the various SQSS reports indicates the consistency of compliance with those standards that define the environmental factors that create the basis for a quality patient experience. The goal in the System is to go green for quality. When that is achieved it becomes easier to practice up to a higher goal as the systematization of the activities automates their occurrence. By watching for trends and patterns in the coloring of the reports, especially the clustering of red boxes, healthcare leaders can identify weaknesses in current operational and patient care systems that allow for undesirable variations in the patient care systems. By making simple modifications to these systems, leadership can tighten up patient care practices to reduce the risk of future errors.

Resilience is the ability of an activity to return to the desired state of performance as quickly as possible after it has drifted. Resilience is an important characteristic of a safety critical environment as the drift away from the desired state often creates the potential for increased risk. In health care, that drift commonly increases risk enough that a provider and patient could find themselves involved in an error that ends in patient harm. The retrospective and reactive nature of health care's traditional approaches to quality monitoring and management have made resilience difficult for many providers as the approaches delay awareness of drift and slow the tightening up of the system weaknesses that could allow a risk to become a repeat harm producing error. The concurrent documentation approach in SQSS along with the immediate availability of trended information and automated alerts that the System generates makes awareness immediate for responsible managers and quality professionals.

The System makes it easier to target those specific enhancements to current systems and patient care practices that will result in timely changes that can lead to greater consistency and reliability while also working to protect the performance potential and productivity of the workforce. Health care has a history of engaging in an approach to quality improvement that resembles aerial bombing. Its data collection activities have been too generalized and have made it difficult to target the specific variables that align making it too possible for errors and quality drift to occur. As a result, health care's quality improvement activities are commonly bigger than necessary—impacting too many people and consuming too many resources while frequently not correcting the original issue. Many times, its traditional efforts have simply introduced new problems.

As the quality assurance reports in SQSS continuously generate "at-a-glance reports", the goal is to make it easier and faster to identify trends and patterns that would be indicative of variables negatively aligning to impact consistency. Knowing where and when these situations are playing out makes it easier to target improvement opportunities that constitute enhancements rather than major changes. Enhancements rather than major changes are important in the healthcare environment as the larger the change, the more time it frequently robs from the patient/provider relationship and has a greater risk of error because of competing demands and distractions. The ability to protect personnel time is becoming increasingly important as it is currently estimated that the average nurse now spends no more that 33% of the work day caring for the patient and 66% of that day completing paperwork that is a by-product of current approaches to quality.

One of the most important goals for health care this decade will be to find ways to raise the bar on quality while protecting the performance potential of the workforce. As an industry that has exhausted its bank of discretionary resources in a financial environment that makes it tough to simply add staff, it will be imperative that the industry finds ways to work smarter as there is very little capacity for its workforce to work harder without negatively impacting the experience of the patient. Supporting the workforce with tools like SQSS and stronger systems that maximize their potential to get things right the first time in resource-wise ways will be an important answer for the industry.

When designed and utilized with the goal of improving the performance potential of the workforce, technology can be one of the greatest enablers that health care can adopt. Additionally, when appropriately managed, the interface between the workforce, the systems designed to support the workforce, and the technology developed to support both can go a long way in protecting the performance potential of the workforce. For health care, that means helping the workforce to more nimbly manage a fast-paced, safety critical environment where it is easy for variables to align and reduce the chance of an optimal outcome for patients.

The performance potential of the workforce is a factor of their performance capabilities and the performance demands placed on them. There is a natural decline in performance potential as performance demands increase. How fast it declines is dependent on the adjustments made to the environment with the purpose of protecting important aspects of performance potential such as productivity. How the work environment is designed to minimize the impact of key human performance factors such as stress, distractions, fatigue and skill deficits impacts an organization's margin for quality. The margin is also impacted by how new performance demands are introduced and managed. These demands are significant for health care in its present environment as it strives to keep pace with healthcare reform, higher patient satisfaction thresholds, changing reimbursement systems, the constant growth of new rules, regulations and outside expectations along with the need to continuously introduce new services and opportunities to advance care as technology continues to change the face of health care.

One of the most important goals for today's providers is to manage all these dynamics that can create negative pressure for the industry's margin for quality in ways that protect the performance potential of the workforce. SQSS is designed to alleviate some of that pressure by using the concept of checklists, computer-based monitoring and automated data management to help organize a multitude of the quality control activities important to health care. It also makes it easier to spread activities out over a larger number of people so as to reduce the stress on smaller groups. For example, most quality control activities in health care have occurred on the day shift because that is when the manager has been present to manually assign and monitor them. The day shift is also the busiest shift of a 24-hour period as it is when the majority of testing and treatment occurs. By having SQSS available to schedule and monitor activities around the clock, managers can more easily assign tasks to other shifts. Health care managers also have a tendency to assign tasks to people they know they can trust to take care of them to reduce the amount of time that they have to invest in monitoring. This practice tends to overload conscientious employees and allows the lesser responsible ones to get away with contributing less. Because SQSS tracks what tasks are getting done by employees and alerts a manager when a task is not done, it is easier to spread out responsibility and create the documentation to drive accountability.

Figure 2:
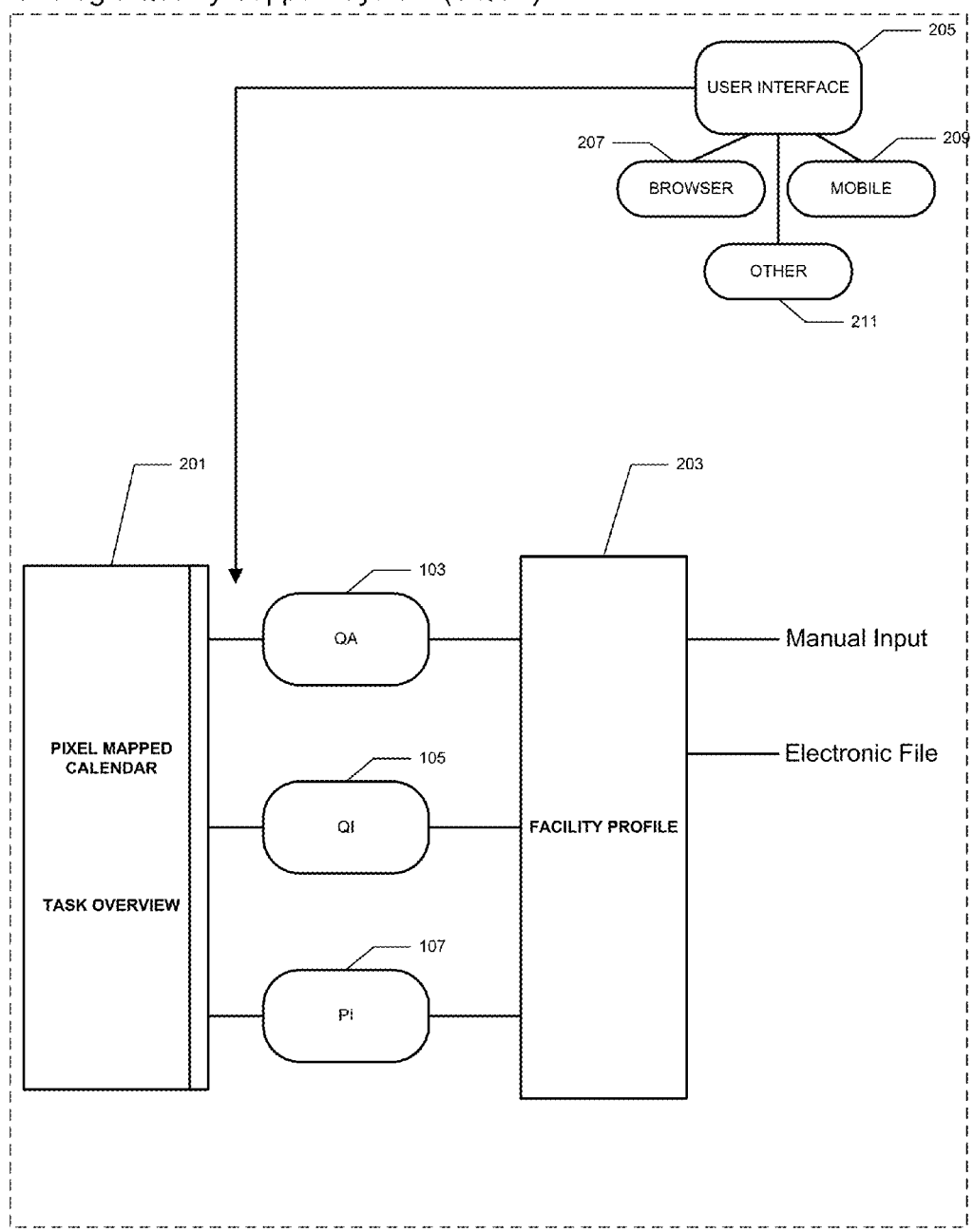
FIG. 2 is a top level input and output diagram of the Strategic Quality Support System.

Turning now to FIG. 2, a top level input and output diagram of the Strategic Quality Support System is depicted. As will be further described herein, each of the major modules is operably connected to a facility profile 203. The major modules being Quality Assurance 103, Quality Improvement 105, and Performance Improvement 107. Other modules may also be present in some embodiments of the present invention. The facility profile 203 contains information related to personnel, staffing, hierarchy, location, and the like. Sources of this information include electronic files and systems as well as manual input by way of human data entry. The Quality Assurance module in turn creates outputs that include a pixel mapped quality assurance calendar, a task overview screen and a task summary screen 201. The major modules, including the Quality Assurance module may be accessed and utilized by way of a user interface 205 that may be web browser based 207, mobile device based 209, or other such techniques 211. Mobile access is particularly value-adding to the Quality Assurance module because it fosters the nimbleness of access to information that makes consistency, resilience and reliability easier to achieve.

Figure 3:
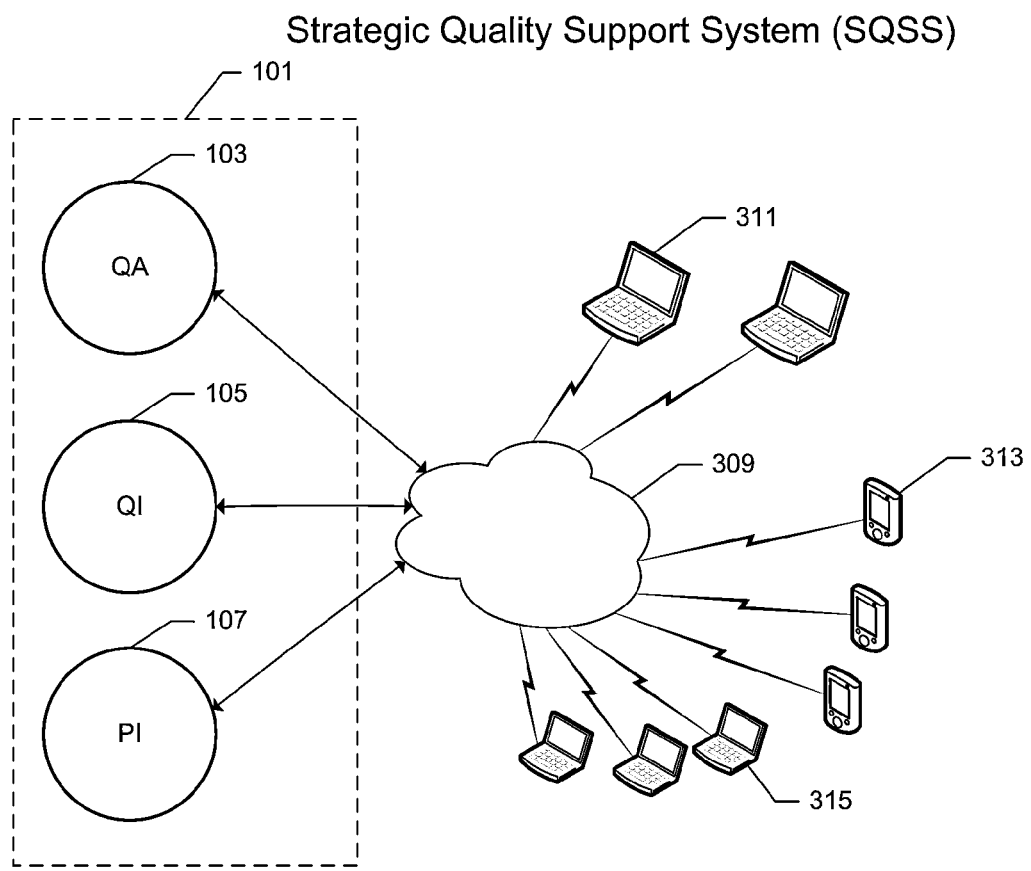
FIG. 3 is a network diagram of the Strategic Quality Support System in use.

FIG. 3 is a network diagram of the Strategic Quality Support System in use. The Strategic Quality Support System 101 is shown having the major modules of Quality Assurance 103, Quality Improvement 105, and Performance improvement 107. Access and utilization of the Strategic Quality Support System 101 may be performed by way of a network 309 such as the Internet or the like. Devices used may include, for example, personal computers 311, handheld devices 313 such as tablets, smart phones, PDAs, and the like, and laptop computers 315.

Figure 4:
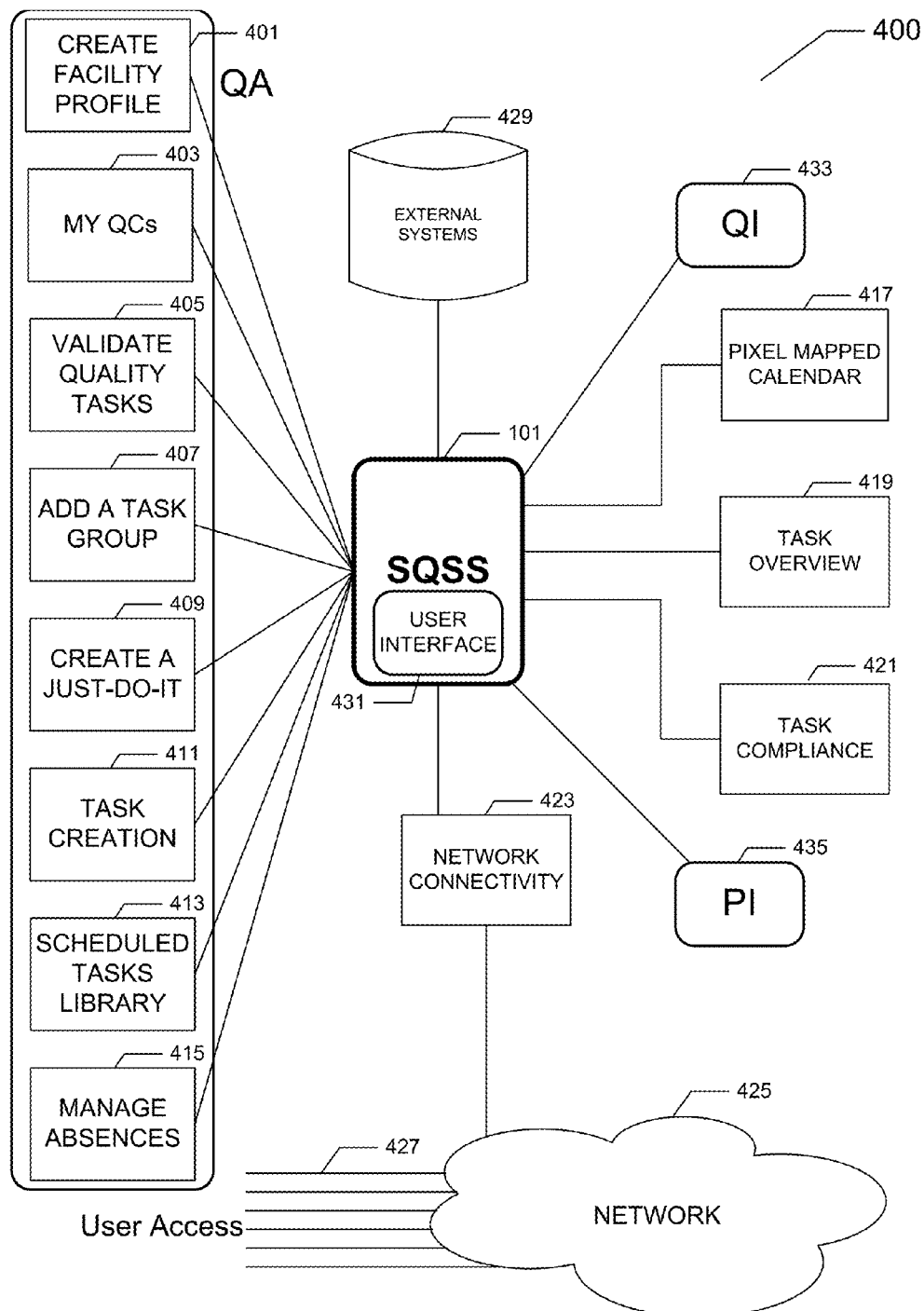
FIG. 4 is a functional block diagram of the Strategic Quality Support System.

FIG. 4 is a functional block diagram of the Strategic Quality Support System that shows the Strategic Quality Support System 101 having a user interface 431. The user interface may be graphical, text based, web based, touch based, gesture based, voice based, or the like. The Strategic Quality Support System 101 may interface with, or receive data to or from, external systems 429. Such systems may include, but are not limited to, human resource systems, payroll systems, hospital or healthcare management systems, project management systems, spreadsheets, databases, on-line education and the like. The Strategic Quality Support System provides network connectivity 423 such as internet or intranet connectivity, through a network 425 providing user access 427. Such user access 427 may be from a computer, a handheld device, a phone, a smart phone, a tablet computer, a laptop computer, or the like.

Various functions are provided by the Strategic Quality Support System 101 that will each be described in greater detail herein. Various functions important to the concurrent management of the day-to-day patient environment are contained in the QA module as depicted in FIG. 4. The first step in using the System is to establish a facility profile 401 that contains the hierarchy and structure of the facility's departments, users, committees and the like. This facility profile is used throughout the various modules of the Strategic Quality Support System 101 and may be entered manually or uploaded from an existing file or files such as a spreadsheet, a database file, or the like. The information contained in the profile is made available in a number of drop-down menus that facilitate creating and managing quality activities that are customized to the facility. For example, the user drop-down menus will contain the names of all the active employees to make it easy to assign tasks to different individuals. The My QCs function 403 provides a user with their quality contributions. This is a list of currently scheduled tasks and allows a user to easily document the status of their responsibilities. The validation function 405 allows for the validation of quality tasks, providing users with a pixel mapped calendar screen that allows them to quickly monitor the health care trends and patterns in oversight activities. A pixel filter provides the ability to sort pixels by status, therefore providing useful information that can be used in managing quality initiatives. The System will automatically schedule validation reviews of all quality control activities. The validation calendar is reflective of the monitoring activities exercised by managers and quality professionals to ensure that activities are being carried out appropriately without quality drift. Adding a task group 407 allows for multiple users to be assigned to a task or a set of tasks. Creating a Just Do It 409 allows for fixing something where the immediate fix resolves the issue, and provides for a means of monitoring and reporting these types of activities. Task creation 411 is accomplished with either a task template or a task wizard. The task is described, scheduled and assigned. The scheduled tasks library 413 contains all of the current standards that are being monitored in the Strategic Quality Support System for an organization. The ability to manage absences 415 are provided for where quality related activities from the My QC list of one person are moved to another trained person when the primary responsible party is absent or for some reason unavailable.

Several outputs of the Strategic Quality Support System 101 can also be seen depicted on the right hand side of FIG. 4. A pixel mapped calendar 417 provides a visual representation of the status of the many quality activities that are occurring or have occurred on each day. For each day on the pixel mapped calendar, a plurality of colored geometries are displayed where each color has significance. Events that are compliant, non-compliant, overdue, current, and future each have a color such as red, yellow, blue, orange, gray and green indicators. Viewing a specified date provides a visual display of numerous colored geometries similar to a display of pixels where trends and patterns can be seen in the overall view of the many colored, geometries in each date. Trends can also be identified over time to discover reoccurring weaknesses. The pixel mapped calendar 417 is stored on computer readable media and graphically displayed on a computer monitor. For the purpose of this specification, a computer monitor includes, but is not limited to, a display on a laptop computer, a desktop computer, a handheld device such as a smart phone, personal digital assistant, tablet computer, handheld computer, or the like. The pixel mapped calendar 417 has a plurality of status indicators for each date; each status indicator being a pixel and being assigned a color corresponding to a current status of a quality assurance task. In some embodiments of the present invention, the pixels further comprise sub-pixels such that at least some of the displayed pixels have more than one color to provide further information regarding current status of a quality assurance task. In some embodiments of the present invention, the sub-pixels are arranged within a pixel such that a secondary color appears as a border around a primary color of the pixel. In some embodiments of the present invention, at least some of the displayed pixels have no color content to indicate that a task is schedule but not due for completion yet. In some embodiments of the present invention, at least some of the displayed pixels have a cross hatching.

A task filtering feature capable of isolating environmental and patient care system weaknesses with minimal keystrokes, and a rapid-cycle calendar-type run chart feature for tracking the progress of improvement initiatives may also be present.

A task overview output 419 provides a report of various tasks assigned to a specific department, committee, user, or month. The task overview contains a visual representation of compliance for each task over a month with a plurality of colored geometries where each color has significance. Events that are compliant, non-compliant, overdue, current, and future each have a color such as red, yellow, blue, orange, gray and green indicators. This allows for timely identification of trends by task and location.

A task compliance output 421 allows viewing the compliance of each task over several months. Compliance percentages are depicted for a historical period, such as, for example, the last twelve months. Its purpose is to monitor for sustainability of an activity and react in a timely manner if drift is identified.

Building on the basics described and depicted by way of FIG. 4, each of the modules and outputs will be described in further detail.

Creating a Facility Profile

To create a facility profile 401 in the Strategic Quality Support System, either a manual method or an automated method may be used. The facility profile contains key organizational information that feeds the functionality of the System. This information includes departments, users, committees, managers, individuals with administrative privileges, and composition of task groups. This is where users, departments, committees, managers and task groups are added and deleted over time to keep the System reflective of the organization.

The first pieces of information that must be added to the System during setup and operation are the departments and users. There are two different methods for adding this information. One method is to add the departments and users to the System one at a time. This method works best once the initial set of departments and users have been added and you simply need to add additional departments and users one at a time. The second method of adding them is via an import using a special upload sheet which allows a facility to upload all departments and users in mass. This is the most effective approach when just getting started in the System and there are a number of departments and users to add.

Figure 5:
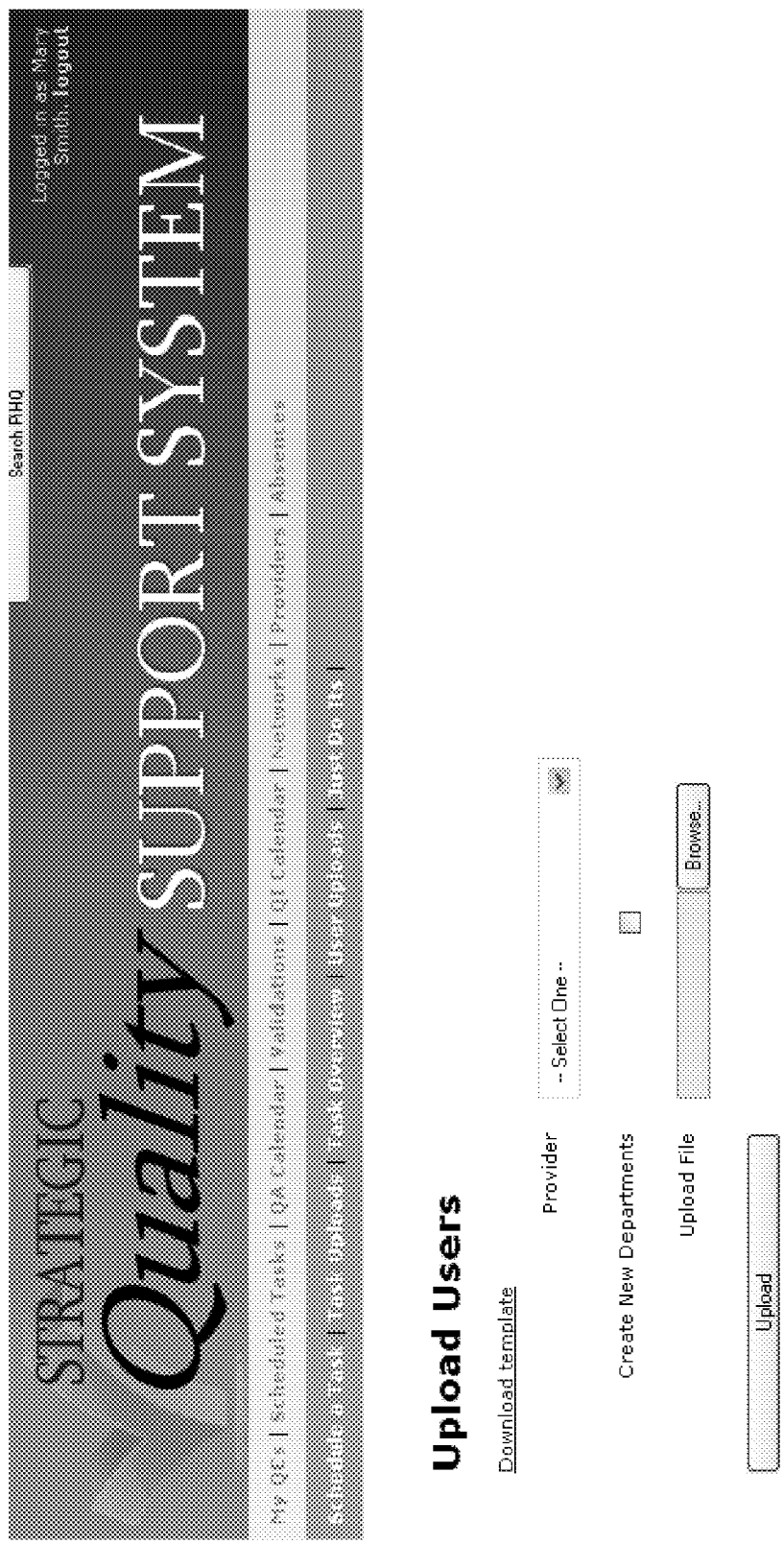
FIG. 5 is a screenshot depicting the upload function.

Once departments and users are added to the System, committees will need to be added and the membership of the committees will need to be established by selecting names from the previously loaded user list. The following instructions detail how to add departments and users using both methods and how to add committees. Turning to FIG. 5, a screenshot of the upload screen is depicted. By selecting download template from the screen, an upload template will open that can be used to add departments and users in mass. The template requires the following information for a successful upload:

Column A—Users First Name—(Required): Enter the users' first names in this column.

Column B—Users Middle Name—(Optional): Enter the users' middle names in this column.

Column C—Users Last Name—(Required): Enter the users' last names in this column.

Column D—Email or Login—(Required): Enter the email addresses for the users' in this column. If a user does not have an email address, a log-in identifier can be entered into this column.

Column E—Users Title—(Required): Enter the job title of each user in this column.

Column F—Password—(Required): Enter a password for each user in this column. The passwords must be a minimum of seven (7) characters with at least one being a numerical value and one being a capital letter.

Column G—Department Name—(Required): Enter the name of the user's primary department of responsibility in this column. A user can be added to multiple departments once he or she is in the System once. During the upload of the initial template, the user is assigned to his or her primary department.

Column H—Provider Admin—(Required): Place a "1" in the rows that correspond to the users that will have administrator privileges. These privileges give people access to all features and report capabilities. Place a "0" in the rows that correspond to the users that should NOT be a provider administrator.

Column I—Manager—(Required): Place a "1" in the rows that correspond to the users that should be a manager. Place a "0" in the rows that correspond to the users that should NOT be a manager. When uploading, a template for a new department, the primary manager of the department is the first person in the list of users to be uploaded. This is important because it loads to the System in several places and makes sure that the managerial e-mails and alerts go to the right person. If another person is to have managerial privileges in the System, such as is seen with an assistant manager, that person is added anywhere in the list with a "1" indicated for "managerial privileges".

When the Template is complete, the creating user saves it to his or her computer. The template is uploaded to the System by:

1. Clicking on "User Uploads" in the green toolbar.
2. Selecting the facility name from the drop down box next to Provider if the user making the upload has privileges for more than one facility.
3. Selecting the option to Create New Departments if departments do not already exist in the System.
4. Clicking Choose File to open a search box to select the user upload template that was saved to the hard drive on his or her computer.
5. Clicking Upload.

If the user upload is successful, a message will appear on the user's "My QCs" page that says Bulk upload of users successful. If the user upload is unsuccessful, a screen will appear that lists the user uploads that have issues and what the problems are. The template will not upload until all the errors are corrected. Once the errors are fixed in the template, upload the template again.

Departments and users can be added to the System one at a time using the following steps. This feature is for the addition of departments and users to keep the profile up to date.

1. Click on Provider in the yellow toolbar. The only users that can see the provider option in the yellow toolbar are those with provider contact, provider administrator and manager positions.
2. If the user looking to add a department or user to the System is a provider administrator, the first screen to appear will require him or her to select the name of the facility to have the addition if the administrator is associated with multiple organizations. This is because the System allows for the management of multiple organizations that belong to larger healthcare Systems as one unit in the System with multiple higher level users. Provider contacts that are only associated with one facility will be taken directly to the screen for adding to the provider profile for his or her organization.
3. A Department is added by:
   a. Clicking on Add Departments under the Department header.
   b. Entering the name of the department in the field asking for this information.
   c. Electing the manager for the department from the drop-down list. This is a required step to save a new department because important e-mails and alerts are required to go to someone. If the manager's name is not in the drop down list, he or she can be added to the System by selecting New User. The new user feature opens a user profile screen where the manager's user account can be created.
4. Clicking Create Department.

Once a department has been created, the name of the department will appear on the Profile page under the header Departments. Clicking on the name of the Department, will open a screen where users and task groups can be added to and created for the department.

To add a user who already exists in the System, the individual with privileges to add users to departments would click on the drop-down box to the left of the Add Users box, select the user's name that should be added to the department and click "Add User". This is also how users are added to multiple departments when their responsibilities cross departmental lines. If a user does not already exist in the System, the individual with privileges to add and create users for a department would select Create User. This opens a screen where a profile can be built for a new user. Using the New User screen, the user's information is entered and Create User is clicked. This will open a screen where a temporary password can be created for the user.

Committees are added to the System by:

1. Clicking on Provider in the yellow toolbar to open the provider profile. The only users that will see the provider option in the yellow toolbar are provider contacts, provider administrators and managers.
2. Selecting Add Committee.
3. Entering the name for the committee to be added.
4. Clicking Edit Member List to add users to the committee.
5. Adding the users to the committee from the user drop down menu.
6. Clicking Update Committee.

My QCs Screen

Turning again to FIG. 4 and the functionality represented by My QCs 403. "My QCs" stands for "My Quality Contributions". Users can think of it as their "to do" list for the day. This will be the first screen users see once they log into SQSS (Strategic Quality Support System). Users are advised to log in at the beginning of their shifts to determine their responsibilities for that day. They are then advised to log in at least once or twice during the shift to document the completion of their tasks. The frequency for documentation is determined by the requirements for demonstrating compliance set by the organization and regulatory standards. For most tasks, the timeframe for completion—doing the task and documenting it—is flexible enough to minimize the number of times users need to access the System in a given shift.

A user will see lour types of tasks reflected on the My QCs screen:

1. My QCs—a list of all those activities that an individual is responsible for on a given day.
2. My backups—any activities that an individual becomes responsible for to help out in the absence of a team member. The System will notify a user with a message at the top of the screen when there are any back-up responsibilities scheduled for the day to minimize the risk that they will be overlooked.
3. My Current Completed Tasks—those tasks that an individual completes will move to this list. This list keeps current tasks available until the task is due again in the event the responsible user needs to go back into the System to document any important changes or additional information.
4. My Validation Events—any activities for which an individual is assigned validation responsibilities. In this role, an individual helps to close the quality loop by verifying that a task is being done properly at some scheduled interval which only the System and the administrator creating the task know.

FIG. 6 depicts a screenshot of the My QCs screen showing a listing of a user's My QCs with the above status indicators and related navigational tools.

There are three responses a user can select when completing a task.

| | |
|---|---|
|  | Compliant—Everything was within required parameters when the task was completed. |
|  | NA—This task is not applicable for today. For some reason, such as the piece of equipment is out of the building for repairs, it becomes impossible or unnecessary to complete the task. |
|  | Non-compliant—Something was identified as being a problem when the task was completed such as a refrigerator temperature being too warm or a defibrillator not reaching maximum charge. These tasks require some type of corrective action. |

Making the proper selection when completing tasks helps the System to generate reports and monitor the resolution of identified concerns.

Marking Tasks Compliant

Figure 7:
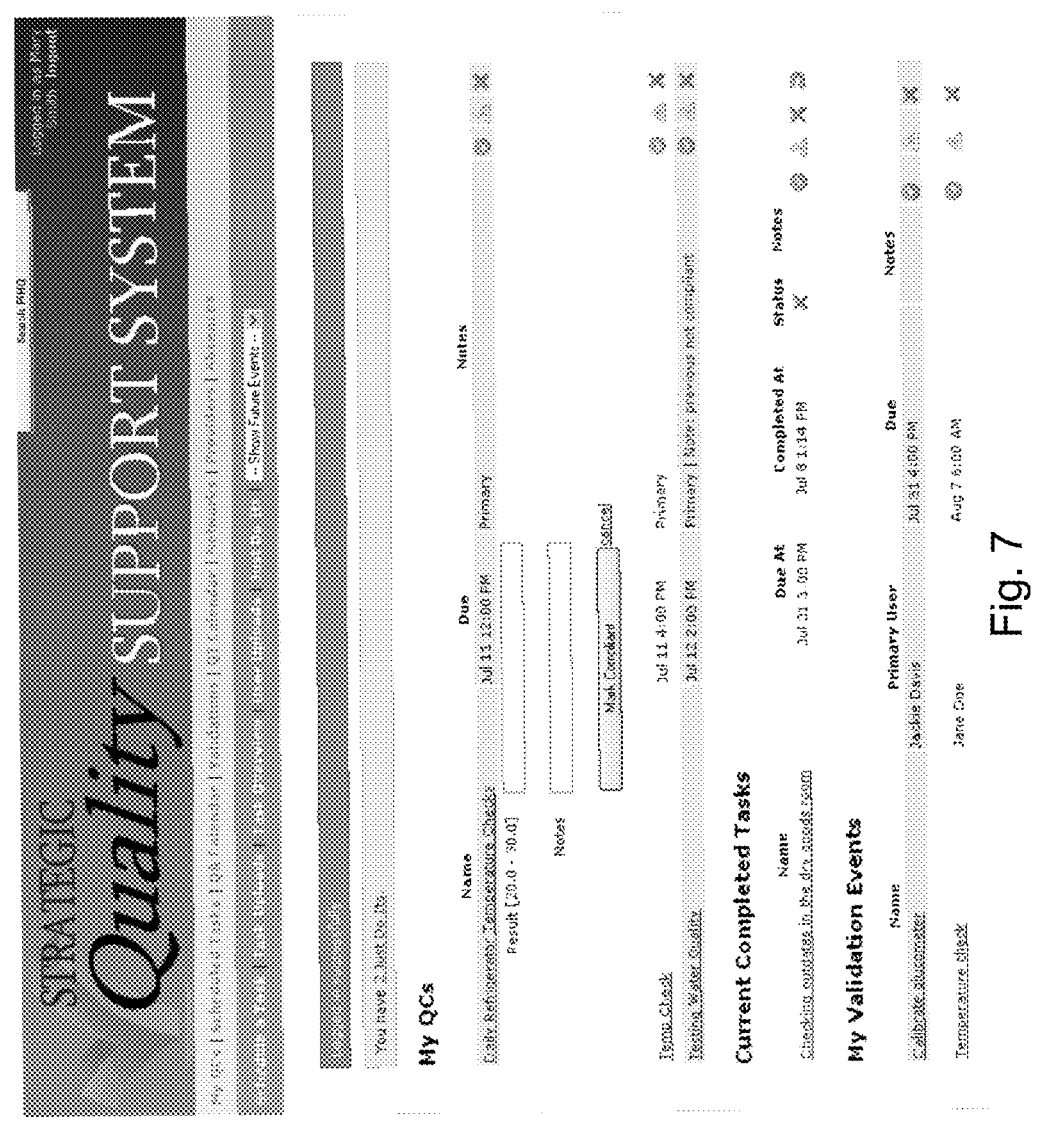

In FIG. 6, the "Daily Refrigerator Temperature Checks" task is due at 12:00 pm on July 13. Once the task is performed, and if the temperature is within the acceptable range set for the task, the task is marked compliant by selecting the green circle (☺). This will open a series of fields where information can be added, as shown in FIG. 7. Some fields will ask for required information such as the temperature. There is also a "Notes" section where other information important to the task can be recorded. Once all the applicable information has been recorded, the user is ready to click "Mark Compliant". The task will move down on the screen to the section titled "Current Completed Tasks".

Marking Tasks Non-Compliant

Figure 8:
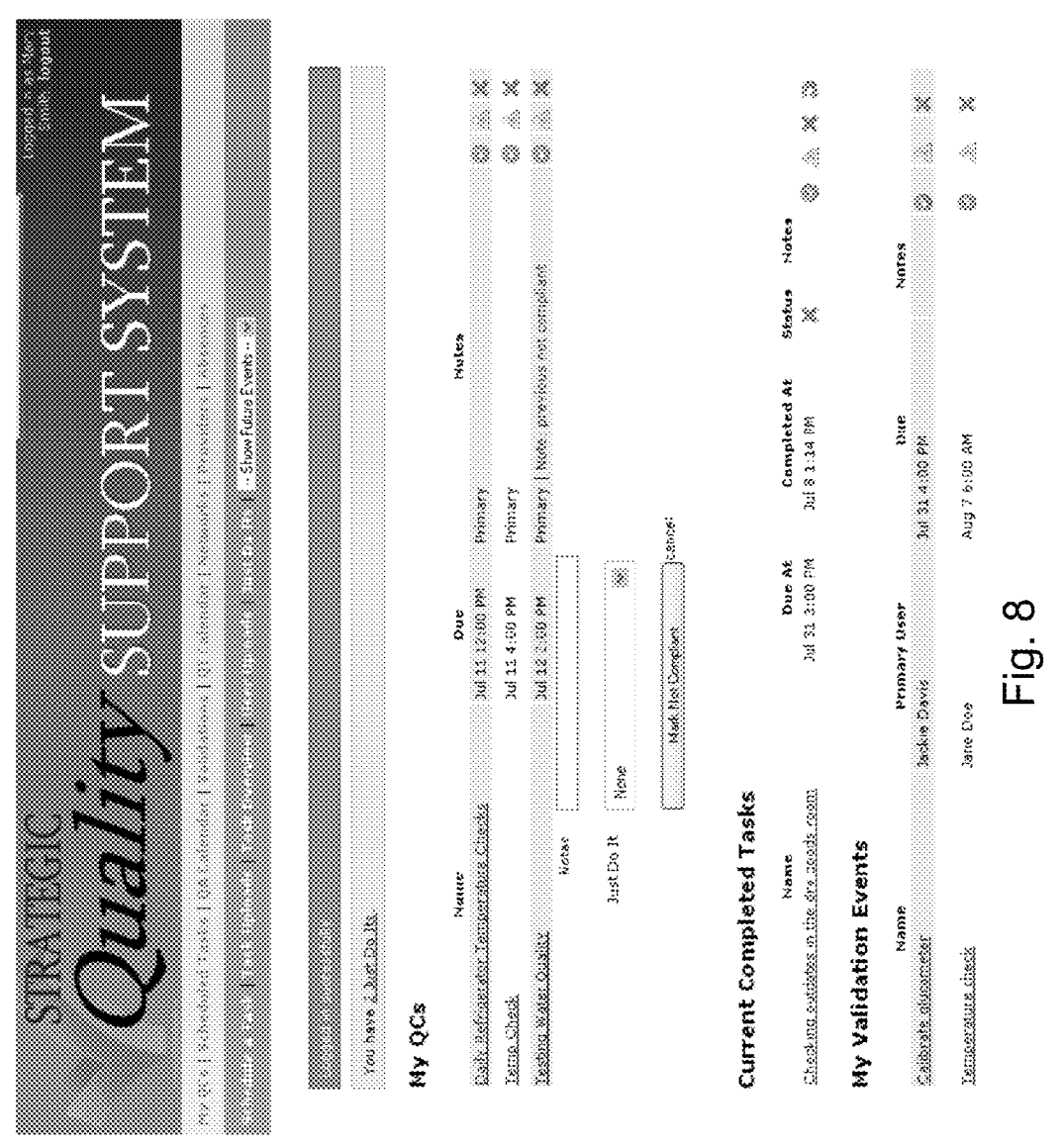

As seen in FIG. 8, when the task is completed and the temperature or some other important variable is out of range, the user should click on the non-compliant symbol (✖). This will open a results area where the temperature for that day can be recorded, a "Notes" section and the option for a "just-Do-It" screen. If the reason that the task is out-of-compliance needs to be referred to another user for resolution, the user can click on the option for "Just-Do-It". If the user can bring the task back into compliance, he can type what he did into the note section and click "Mark Non Compliant". Marking it non-compliant even though the fix was immediate makes it easier to track for trends that indicate the need for a bigger action. For example, consider a refrigerator that is consistently too warm because the seal on the door is bad and the door won't stay closed. Having the staff repeatedly have to close the door as a corrective action is not good for food or medication integrity. A trend of these types of notations associated with a refrigerator that is repeatedly too warm would serve as an indication that a more effective corrective action is needed.

Marking Tasks Not Applicable

Figure 9:
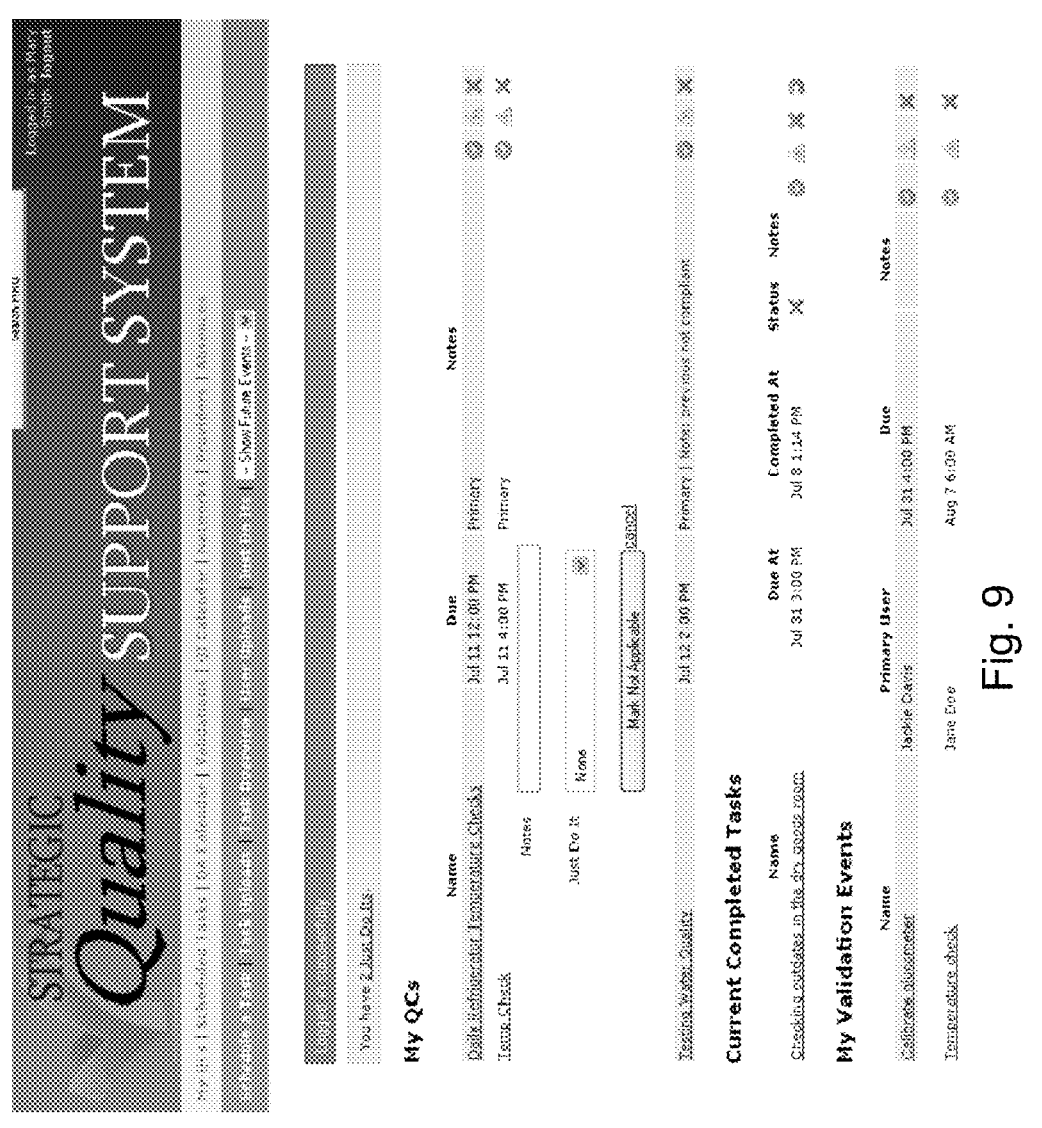

Some tasks that are scheduled, especially those scheduled for every day, may periodically not be applicable for a variety of reasons. For these tasks, the responsible person would mark it "Not Applicable" by clicking on the N/A symbol (⚐) and recording the reason the task was not completed as depicted in FIG. 9. Some of the common reasons where this might apply are:

The task only has to be done when the responsible person is present.

A piece of equipment might be out of the building being repaired.

A task may not be required if a related task does not occur. For example, water temperatures and poundage of laundry do not have to be recorded if no laundry is done.

When "Not Applicable" is the selected choice, it is required that the responsible user indicate in the notes section why the task was determined to be N/A.

The System also allows a user to mark tasks N/A into the future. For tasks that will not apply during vacations and other situations where it is known in advance that activities will not have to occur, a user can click on "Show Future Events" in the light green toolbar and select how far out into the future he or she would like to see—one day, two days, one week, or two weeks, as seen in FIG. 10. A list of all tasks scheduled during that period of time will appear with a N/A symbol (⚐) next to each one. The user can then click ⚐ next to the tasks that do not need to happen, record the reasons for the N/As and click "Mark Not Applicable". This should only be done on tasks that do not need to occur. An user should not mark tasks N/A when the failure to perform will go against current regulations or important rules of quality. For example, there is a regulation that a generator must be fired up once a week to guard against a system failure if there is a power outage. The fact that the individual assigned this responsibility is on vacation does not negate the need to perform the task. That is why SQSS allows for the assignment of a back-up responsible party.

Making a Change to a Completed Task

As an individual completes tasks, they will disappear from the "My QCs" list and reappear under "Current Completed Tasks". Completed tasks will stay under Current Completed Tasks until that task comes due again. For example, if the task that has been completed is a daily task, it will stay under Current Completed Tasks until 11:59 pm of the current day. However, if a task is a monthly task that is due on the last day of the month but it is completed earlier in the month, it will appear under Current Completed Tasks until the start of the next month that it is again due. For example, if a monthly task is due by April 30$^{th}$ and completed on April 14$^{th}$, the task will stay on the Current Completed Tasks List until the end of April. This feature exists to allow users to make changes and additions to documentation fields during the period of time that rules of compliance allow for it.

For example, under Current Completed Tasks in FIG. 6, you can see that "Checking outdates in the dry goods room" for the month of April has already been completed and was marked compliant as indicated by the  in the status column. The status can be changed by clicking on one of the three selections to the right of the status column. For example, if the status of the task was incorrectly marked compliant and needs to be changed to non-compliant, the responsible user can change the status by clicking on the  . This will open any notes that were documented when the task was previously completed and allow for additions or edits. The user can also select the option to create a Just-Do-It screen if an action was taken to bring the task back into compliance. The responsible user can then click the Mark Non Compliant button to change the status. The  in the status column will change to  .

Back Up Responsibilities

If a user has been listed as a "Back Up" on any tasks, the tasks will show up in the "My QCs" list when the responsible party is marked absent. The back-up user will be notified if any back-up tasks have been moved to his or her "My QCs" list by a notice at the top of the page. Also, any tasks that have been moved to a back-up partner's "My QCs" list will be identified with a note that says "Backup" next to the added task.

My Validation Events

Users can also be assigned as a validator of tasks. Validation activities are designed to help close the quality loop of identifying, doing and verifying. They help to guard against quality drift in highly dynamic and fast paced environments. They also allow for the early identification and remedy when an individual may be doing a task with the best of intentions but doing it wrong. If a user has been assigned a validation activity, his or her responsibility is to verify that the task is actually occurring and occurring correctly. Validations are not terribly timely or difficult, but are very important in patient and employee safety. Tasks will show up under "My Validation Events" when it is time to validate them. Rather than people having to mentally remember to check the multitude of things in a health care organization, the System is designed to do that for them. Tasks will appear under "My Validation Events" at the beginning of the month that they are scheduled to occur and stay on the list until they are completed. This feature allows for flexibility in getting them done while minimizing the risk of predictability if gaming quality responsibilities is a possibility. The unpredictability of when a task will be validated makes it easier and more effective to ensure that the task is being done correctly every day—not just on the days people know it is being checked. If the validation is not completed within 30 days of appearing on the My "QC" screen, the System will send an alert to a higher responsible user.

Documenting a validation activity in the System is as simple as indicating that it was "Compliant" or "Non-compliant". When either one of these are selected, a field for recording "Notes" will open. This is where the validator can record what he or she did to validate the activity, any pertinent findings from the reviews and any recommendations that were made to the staff to strengthen the activity. This documentation can then be reviewed at the next committee meeting for the purpose of fulfilling oversight responsibilities and identifying opportunities to strengthen the systems designed to support the staff in getting activities right the first time.

Turning again to FIG. 4 and the validate quality tasks module 405, validation activities are integrated within the Strategic Quality Support System 101.

The validation feature of Strategic Quality Support System (SQSS) 101 provides a user-friendly mechanism for ensuring that quality control activities are occurring correctly and yielding the desired outcomes. Health care is an industry at great risk of quality drift as the pressures of the present environment make shortcuts seem like viable options to growing lists of responsibilities and pressures. While the shortcuts may seem to save steps and minutes in the short term, they cost in the form of regulatory penalties and patient harm.

Quality drift occurs when a quality control activity important to ensuring the integrity and safety of the patient care activity or a safety critical environment does not occur, only partially occurs, or does not occur in a way that offers the protection intended. It commonly occurs when the responsible parties feel overwhelmed or fail to recognize the value of the activity. The latter tends to take place after long periods of time where errors or near misses do not occur. This fosters a false sense of security that causes people to start to questioning whether quality control activities are truly important. In these instances, quality tends to slowly and insidiously drift until the shift away from the original safety measure is significant enough to allow variables to align so that an error can occur.

Validation reviews are intended to help guard against quality drift and to make it easier for managers, quality professionals and leaders to fulfill their responsibilities of overseeing the integrity and safety of the patient care environment. It systematizes oversight responsibilities into a series of checks and balances so to minimize the risk that something will get overlooked and people will not be aware of the drift until it hurts a patient or the organization. Today's fast paced healthcare environment is full of distractions. These distractions make it easy for managers, quality professionals and leaders to have the best of intentions to monitor their environments but not fulfill those intentions as other demands draw their attention away.

SQSS is designed to schedule administrative validation reviews based on risk and prior experience. The System tracks the day-to-day activities of the frontline staff in fulfilling their responsibilities to perform the tasks while coordinating and tracking validation to ensure the accuracy and appropriateness of those activities. Performing the tasks (My Quality Contributions—My QCs) and validating those tasks are two very different types of quality control activities. My QCs are the day-to-day quality controls that ensure the integrity and safety of the environment. Validation reviews are retrospective reviews that occur periodically to close the quality loop by being able to "validate" the integrity of the quality control activity. They create the environment where a healthcare organization does not have to rely on outside surveyors to tell it whether or not it is in compliance with important safety standards. It also overcomes the risks associated with the fact that familiarity with a process can prompt important signs and symptoms to be overlooked.

Validation reviews are generally assigned in the System to managers, senior leaders and quality professionals. The System does not allow people to validate their own work. The goal is for people to help one another in ensuring the integrity of the environment and patient care activities by bringing a fresh set of eyes to the process to catch slips that might be overlooked by the person involved in the process. It is not about catching people doing something wrong—it is about protecting one another in an environment that makes it easy for the most conscientious people to fail.

Validations are scheduled in the System at the time a task is created. The last screen in the Task Wizard asks for:

1. The committee that will coordinate the administrative oversight function. As committees are an important way for system-wide policies and procedures to be established and many quality control activities cross multiple departmental lines, healthcare committees tend to provide important input into the design of organization-wide quality activities. The Validation Report for the System is designed to help committees target needed enhancements to structures and systems.
2. The individual who will perform the validation review. This is normally a manager, quality professional or senior leader. The integrity of the process is easier to argue on outside survey when the validating individuals are not the same individuals who have day-to-clay responsibility for the activities. For example, it is easy to argue stronger checks and balances when the quality director does validations for the pharmacy than if the pharmacist validates his own department or if nursing validates for pharmacy and pharmacy validates for nursing. It is similar in concept to the financial safe guards of not having the same person who collects the money be the person who deposits the money and records the transaction. It is not about trust as much as it is about being able to objectively defend the process and minimize the temptation for shortcuts.
3. The frequency with which the validation will occur. The choices in the System are monthly, quarterly, bi-annually, yearly and same as due date. The frequency is dependent on a number of variables. Validations should align with the frequency of the scheduled task. For example, there is no reason to validate more than annually if a task only has to occur once a year. Some of the considerations in determining how often to validate are:
   a. The risk for harm associated with quality drift. The greater the risk of harm or drift, the more frequent the task should be validated. For example, it is important to validate the procedure for checking the temperature on the blood bank cooler more frequently than the employee food refrigerator.
   b. Unique variables that can increase the risk of drift. For example, a leader would want to validate activities in a patient care area with frequent agency staff more frequently than an area with long term stable staff. Activities assigned to a new employee should be validated more frequently until he or she has settled into his or her new position. These validation reviews can be valuable documentation in completing the initial probationary evaluation that determines if an employee is a good fit for a safety conscious culture.
   c. Tasks new to the facility should be validated frequently until leadership is comfortable that the staff has adopted the new behaviors as habits.
   d. Tasks that are known problems should be validated more frequently until systems can be relined in ways that make it easier for the workforce to get it done.
   e. Tasks that are under revision as part of a quality improvement activity could be validated more frequently during the period of change. Please note that these validation activities can easily become part of the data for tracking the progress of the improvement initiative.

Validation reviews are not a substitute for the scanning that is a normal piece of management. Scanning is a management practice of being aware of one's environment at all times. For managers, it is being aware of the integrity and safety of the areas they are responsible for. One of the most important responsibilities of a manager is to make sure that the area of a healthcare organization they are in charge of maximizes the chances that their staff will get their responsibilities right the first time and minimizes the risk that an error can occur that will hurt a patient, employee or the organization. The Navy refers to this skill as "having the bubble."

For example, a nursing manager may quickly pick up the crash cart checklist as she walks past the crash cart to make sure it is getting checked as required or quickly scan the narcotic count book as she is in the medication room doing something else, or double check the care plans for updates as she is waiting on the phone. Scanning is the quick and continuous checking of the environment by the manager to make sure that day-to-day operations are as they should be. Another example of scanning is quickly looking at the pixel mapped quality assurance calendar and other at-a-glance reports in SQSS for their transition to green and for trends and patterns that may indicate system weaknesses.

Validations differ from scanning in that validations are more episodic and are part of the quality cycle in ensuring that all quality control activities are reviewed as part of a series of checks-and-balances. It is a practice common to safety critical environments where harm or fiscal impropriety, no matter how great the intentions to do things right, is a risk because of the dynamics of the environment. Managers scan to manage their environment while organizations validate to ensure the integrity and safety of the environment. Together, scanning and validating protect everyone in the organization by fostering reliability and resilience of the healthcare environment.

Validations appear on the bottom of the "My QCs" list for managers, senior leaders and quality professionals. They are part of their "Quality Contributions." Validation reviews show up on a "My QCs" list based on the frequency set when the task was set up. See FIGS. 6-10. They are active on the list for thirty days before the System sends an alert. The design allows validators to do these activities when they have time and in a manner that makes them unpredictable. Validations are simple activities and it is important to not make them any more complicated than they need to be. The goal is to validate that the activity is happening, it is being done properly and it is yielding the desired outcome. For example, a validation review for a daily refrigerator temperature check would include verification that it has been occurring daily since the last validation, it is being done properly (the thermometer is properly placed) and the temperatures since the last validation have been within the requirement range to protect the integrity and safety of the medications stored in the refrigerator.

Validation reviews are recorded the same way as quality contributions. They are compliant—, not applicable  or non-compliant . The notes section is a good place to document any recommendations that might have been made to the workforce to strengthen the integrity of the quality control activities during the validation review and recommendations to the oversight committee regarding ways to strengthen the approaches to patient care being validated. These notes can then be discussed as part of the next oversight committee meeting where minor changes to processes might be made to make them even more reliable and resilient.

The failure of health care to be able to demonstrate good control over its environment is one of the primary reasons that the regulatory environment has been growing and the public's confidence in the industry has declined. As the expectations for transparency grow and younger generations of patients ask tougher questions about their risks in different patient care environments, the ability to demonstrate strong systems of checks and balances will become increasingly important in demonstrating a provider's commitment to quality and safety. The Validation activities in SQSS have been designed to create the needed environmental quality control and documented evidence that can be important in demonstrating a provider's commitment to quality.

Adding Task Groups

Turning again to FIG. 4 and the Add A Task Group module 407, multiple users can be assigned to a task or set of tasks. This feature is great for tasks that are completed by staff that can change from day-to-day. Health care's struggle with how to manage the challenge associated with a team approach to tasks is one of the primary reasons it has been unsuccessful over the years in strengthening its approaches to quality through systematization. For example, if you have tasks that are due seven days a week but the responsible party is dependent on which individual is scheduled to work each day, you cannot have one person assigned as responsible for the task(s). A case where this would apply might be the checking of refrigerator temperatures that is assigned to the position of "nursing assistant". It would not always be the same nursing assistant but it is important for leadership to know which nursing assistants are and are not following through on the task when they are working.

The Task Group feature allows this activity to be easily managed by assigning these types of tasks to a Task Group. In this situation, tasks will appear on the My QC lists of each user that belongs to the selected Task Group when the task comes into the reminder phase. The task will only need to be completed by one person in the group but everyone in the group will be able to see it. Once one user completes the task, it will disappear from all of the other My QC lists and the System will record which group member completed the task.

Figure 11:
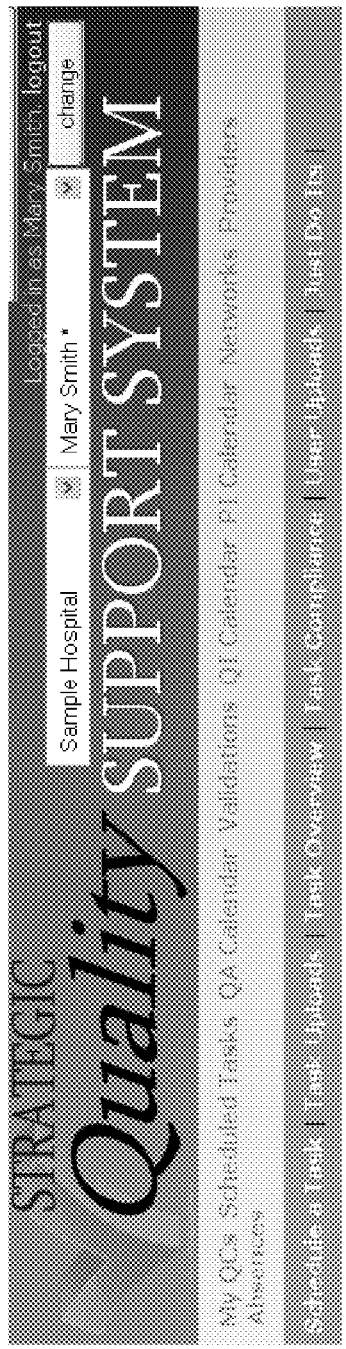
FIG. 11 is a screenshot depicting the providers screen.
Figure 13:
FIG. 13 is a screenshot depicting creating a new task group.

To use this feature, the Task Group must first be created. To do this, a user would:
1. Click on Providers in the "yellow toolbar" as seen in the screenshot of FIG. 11.
2. Click on the department that the task group will be assigned to, as seen in FIG. 11.
3. Click on Add Task Group, as seen in FIG. 12.
4. Name the task group and click "Save", as seen in FIG. 13.
5. Once a user clicks "Save", a screen will open that will allow the user to select the users that will belong to this task group.

Any users that are assigned to the responsible department will be in the drop down list. Once a user has reached this point, the task group has been created and tasks can be assigned to it. The name of the group will appear in any user drop-down Menu just like the name of the individual employees. To assign a task to the task group, a user would select the task group as the responsible party. For example, the task wizard that is shown in FIG. 5 is for establishing a task for checking crash carts. The nurse manager wants to assign this task to the task group titled "Staff Nurse" so that all staff nurses in that task group will have the ability to complete the task and mark it off. To do this, simply select "Staff Nurse" from the list of users when assigning primarily responsibility.

When the task comes into the reminder phase it will appear on every group member's My QCs list. The entire group will get credit for the task completion (indicated by a green box on each employee profile) while the group member who completes the task will get special recognition for it on his or her individual profile that the System can generate. It will appear as a "green box with an X through it" on the profile. If no one in the task group completes the task, everyone in the group will get credit for the incomplete. It will appear as a "red box" on the individual profile for each member of the task group. This feature is designed to promote greater teamwork at the staff level. The goal is for the people working together to help judge who will do different tasks based on workload. For example, if three nurses are working and one has a lighter assignment than the others, the three nurses might agree that the nurse with the lighter load will take care of the quality control tasks that day.

Turning again to FIG. 4 and the Create a Just Do It module 409; a Just Do It is one of two types of quality improvement activities common to an effective quality program. Unlike improvement initiatives that require the modification of a system to yield more effective ways of getting work done. Just Do It activities focus on fixing something where the immediate fix resolves the issue. Health care, like many industries, have many quality control activities that periodically are in need of a Just Do It to bring the activity back to a state of desired performance. For example, a walk in cooler may become too warm because a cooling coil springs a leak. Once the leak is repaired and the system is recharged with refrigerant, the cooler returns to the desired temperature range.

Reporting and tracking these types of activities has always been a challenge for industries as complex and fast-paced as health care. It has often required time consuming and paper intensive approaches where people have to take time to fill out a form, the form has to be delivered to another department, a report of repair needs to be completed and the repair needs to be communicated by phone, paper or e-mail to the party who generated the concern. The resource-intensive approaches have always made it easy for safety-critical issues to get lost or overlooked and take people away from value-adding activities. The Just Do It feature in SQSS makes it much easier and less resource intensive to manage these types of quality improvement opportunities as the System allows staff to simply move concerns to the "My QCs" list of other individuals when compliance concerns are identified. The documentation trail for the correction can then be maintained in the System with a few very simple entries.

A Just Do It is most commonly generated when a task on a "My QCs" list is found to be non-compliant as in the example above when the walk-in cooler is found to be too warm and cannot be resolved by the individual who identities the concern.

To create a Just Do It, a user would:
1. From the My QC list, mark the task that is out of compliance—Not Compliant—by clicking on the red ✖. This will open a "Notes" section and the option to create a Just Do It.
2. Complete the pertinent information for the task:
   a. Type a numeric entry if it is required such as the temperature of the cooler.
   b. Type any notes that may be pertinent to what was found when the task was completed. The System stores this information to be used to generate reports.
   c. If the issue is one that must be referred to another individual or department for resolution, select "Create New" from the Just Do It drop-down list.
   d. Click Mark "Not Compliant". This will record the activity as a blue box on the pixel mapped quality assurance calendar as an alert of non-compliance with some current standard, record any pertinent information to the appropriate logs in the System and store the information for future reports.

Once a user clicks the "Mark Not Compliant" button, the screen for creating a Just Do It will open. The user would then:
 a. Create a brief title-type description for the problem that is being referred to another department. This title lets the person receiving the referral quickly know the issue to be addressed.
 b. Provide a detailed enough description in the "Description" box to let the person receiving the Just Do It knows what was found and any corrections that were attempted before the referral was made.
 c. Assign a severity code to the concern. The options are safety critical, safety ASAP, near miss and great catch. The severity code helps to prioritize corrective action plans and sets the window of time that the System allows for a concern to be addressed before alerting a higher user. For example, the System sends e-mail alerts every two hours to the responsible party and the quality director for safety critical concerns because of the risk the issue creates for patient harm if not addressed immediately. It allows six hours for activities labeled safety ASAP, twenty-four hours for those categorized as "near misses" and seventy-two hours for great catches. Once the Just Do It is created, the user, clicks "Save". The Just Do It will be created and the notification of the new Just Do It will be sent to the manager of the department that it is being referred to. When the manager of that department logs into his/her "My QCs" list next, there will be a notification at the top of the screen that he or she has a new Just Do It that needs to be addressed. For safety critical and safety urgent issues, the System will also send an e-mail and indicates the urgency in the message bar on the "My QCs" list. For safety critical issues, the System will send reminder e-mails every two hours until the issue is addressed in the System.

Users can view the new Just Do It by clicking on the blue link in the message bar that appears at the top of the "My QCs" list or can view any previously created Just Do It activities by clicking on the Just Do Its title in the green tool bar. This will open the log of all current Just Do It activities that have been referred to a manager or have been referred to another department by that manager and his or her staff.

Figure 14:
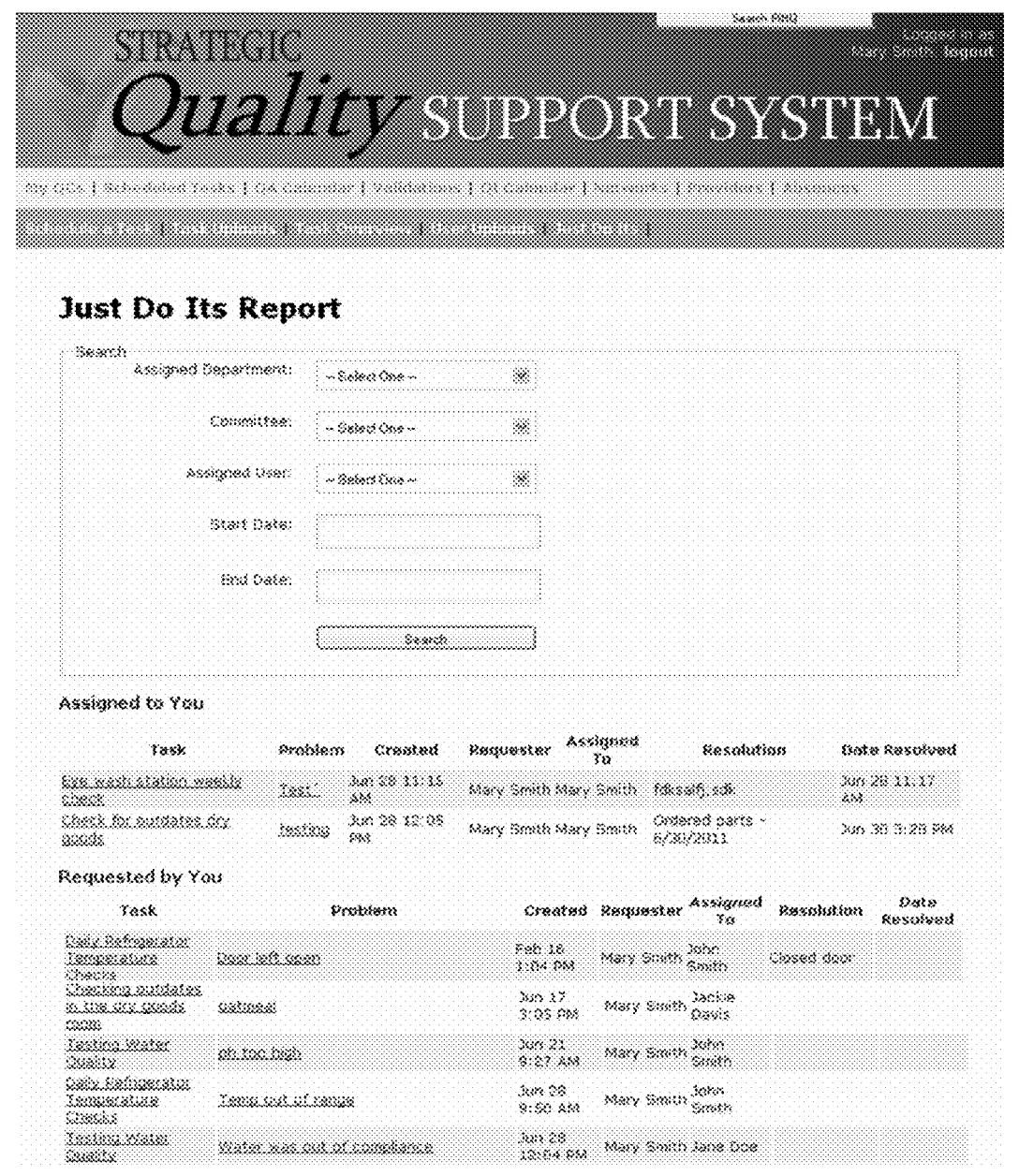

Any non-compliant tasks assigned to a user will be listed under the header titled "Assigned to You", as depicted in FIG. 14. Those non-compliant tasks referred to another department by a user will be listed under the header titled "Requested by You". Non-compliant tasks referred by an employee of a department will be listed under the header titled "Managed by You". As non-compliant tasks are resolved, they move under a header titled "Resolved by You".

Figure 15:
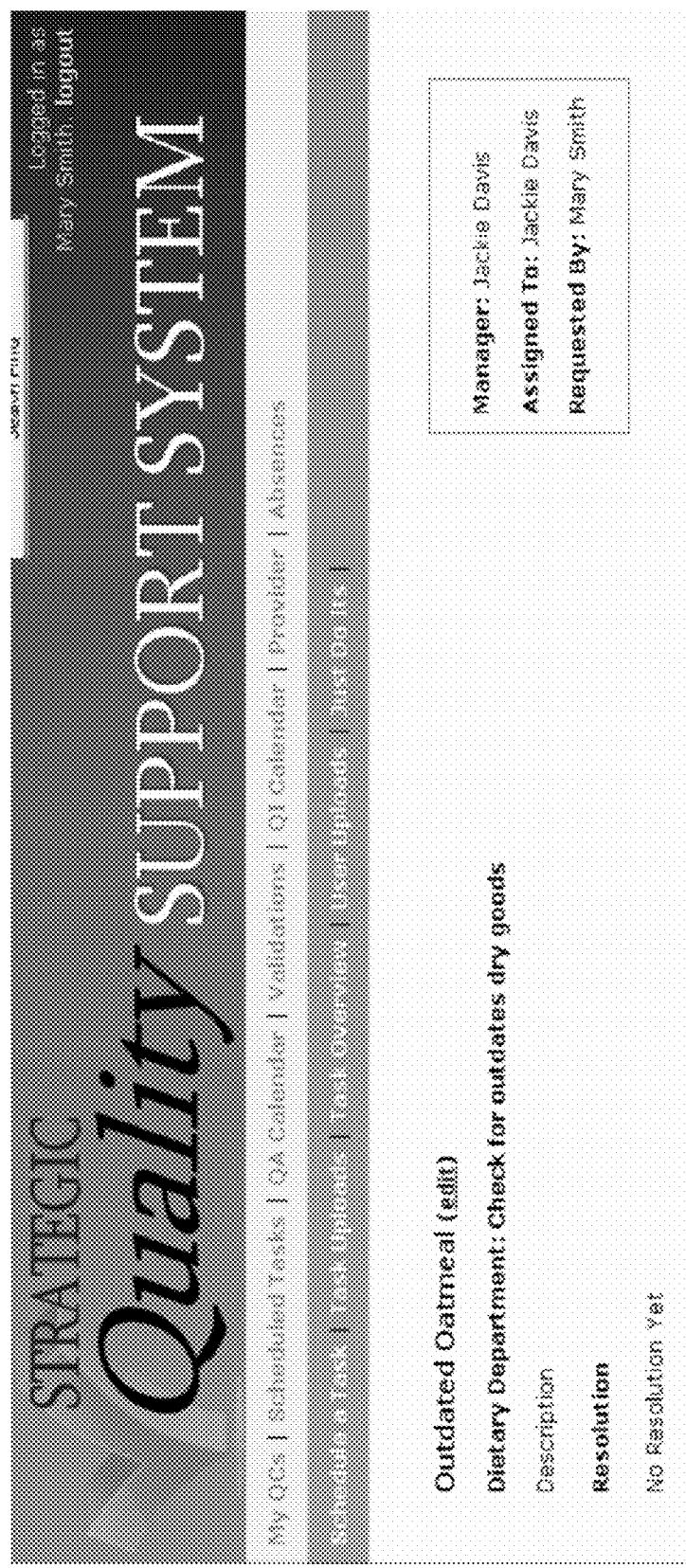
FIG. 15 is a screenshot depicting a Just-Do-It edits screen.
Figure 16:
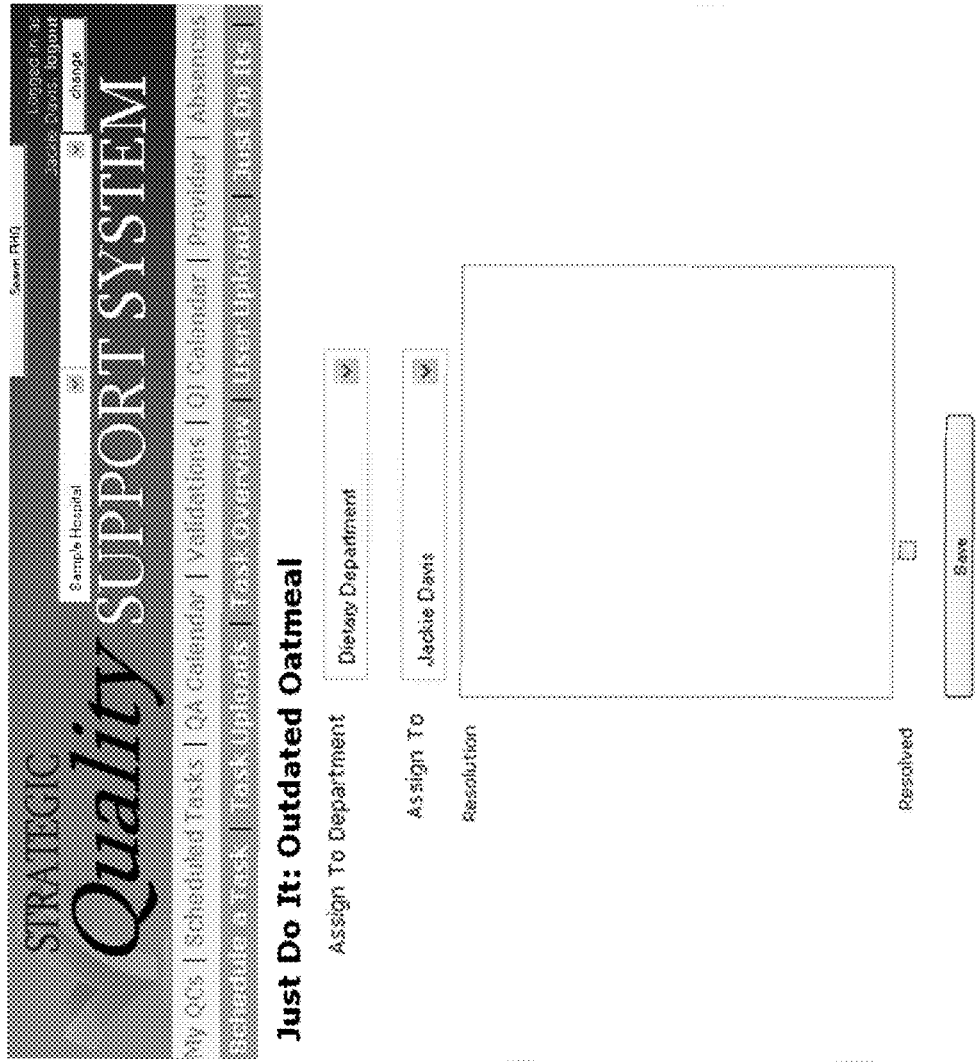
FIG. 16 is a screenshot depicting a Just-Do-It summary screen.

To edit, resolve, or reassign the Just Do It, a user would:
 a. Click on the problem title in the Problem column. This will open a summary of the Just Do It, as seen in FIG. 16.
 b. Click on "edit" next to the problem. This will open the edit screen, as seen in FIG. 15. A set of drop down boxes will open which will allow the manager to refer the issue to another department, move it to the "My QCs" list of one of his or her employees or indicate that the issue has been resolved, as can be seen in FIG. 16.

The edit screen for a Just Do It can be accessed more than once. There are many Just Do It activities that cannot instantly be resolved because parts need to be ordered or a specially skilled repair technician needs to be called in. If the repair is going to be delayed, it is important to note in the System the steps taken to protect the patients or the integrity of the process during the delay. These types of chronological notes can be recorded in the Resolution Box. The individual who made the referral can then see the notes when he or she accesses the list of Just Do It activities they have referred to others and can track the progress of the resolution without having to bother the staff working on it.

Once the issue is resolved, the box next to "Resolved" is selected and the date of resolution is automatically recorded in the log under the "Date Resolved" column.

Figure 18:
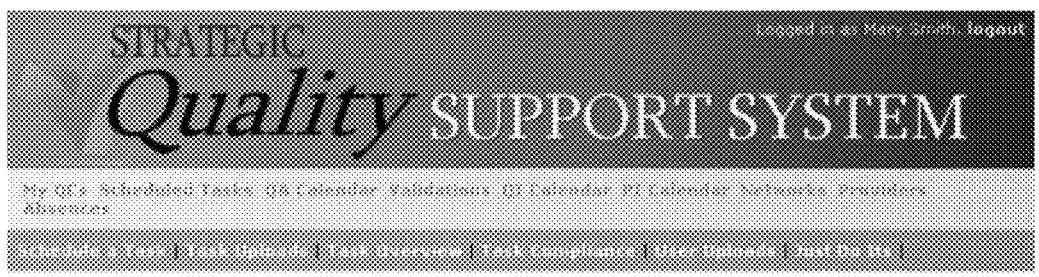
FIG. 18 is a screenshot depicting a Just-Do-It prioritization reporting screen.

FIG. 17 is a screenshot depicting a Just-Do-It severity prioritization screen and FIG. 18 is a screenshot depicting a Just-Do-It prioritization reporting screen.

A Just Do It can be assigned to the same department as the employee making the referral. As SQSS is designed to work directly with the frontline staff to facilitate getting day-to-day quality control activities done, there will be times when the person who has to resolve the issue will be the manager of that department. If a staff member creates a Just Do It that needs to go to his or her own manager, he or she can select his or her own department when creating the Just Do It. This again saves the time of having to find and report the activity to a manager or interrupting the manager when he or she is involved with another issue. It reduces the likelihood that an activity will get forgotten or lost at the same time it protects the productivity of the workforce.

The Just Do It activities can also convert to system enhancements that are managed inside the rapid cycle Quality Improvement Calendar. If an activity keeps coming up as a Just Do It, it will be important to analyze it as a potential system failure rather than an isolated event that simply needs to be fixed. Fixing the same issue over and over with the same band-aid is a poor utilization of resources and increases the risk of a non-compliance eventually resulting in patient harm. When a manager analyzes a Just Do It that is referred, he or she may determine that it is actually a system failure that should be addressed by strengthening the system rather than applying a band-aid. System enhancements are managed in the Quality Improvement Calendar discussed later in this specification.

Creating Tasks

Turning again to FIG. 4 and the Task Creation module 411, tasks can be created in the Strategic Quality Support System 101 using the Task Wizard or the Task Template. The Strategic Quality Support System 101 allows users to create tasks in the System using two different methods. The first method uses the "Task Wizard" to allow users to build one task at a time. The four primary activities in building a task are:
 1. Giving the task a name and description.
 2. Scheduling the task.
 3. Determining who will be responsible for the task.
 4. Determining who will validate the task to close the quality loop of identifying, doing and verifying.

To open the Wizard, a user would click on "Schedule a Task" in the light green toolbar. This will open the Task Description screen, which is the first of four screens in the wizard. Task creation may, in some embodiments of the present invention, be limited to certain user classes such as, for example, administrators or managers.

Figure 19:
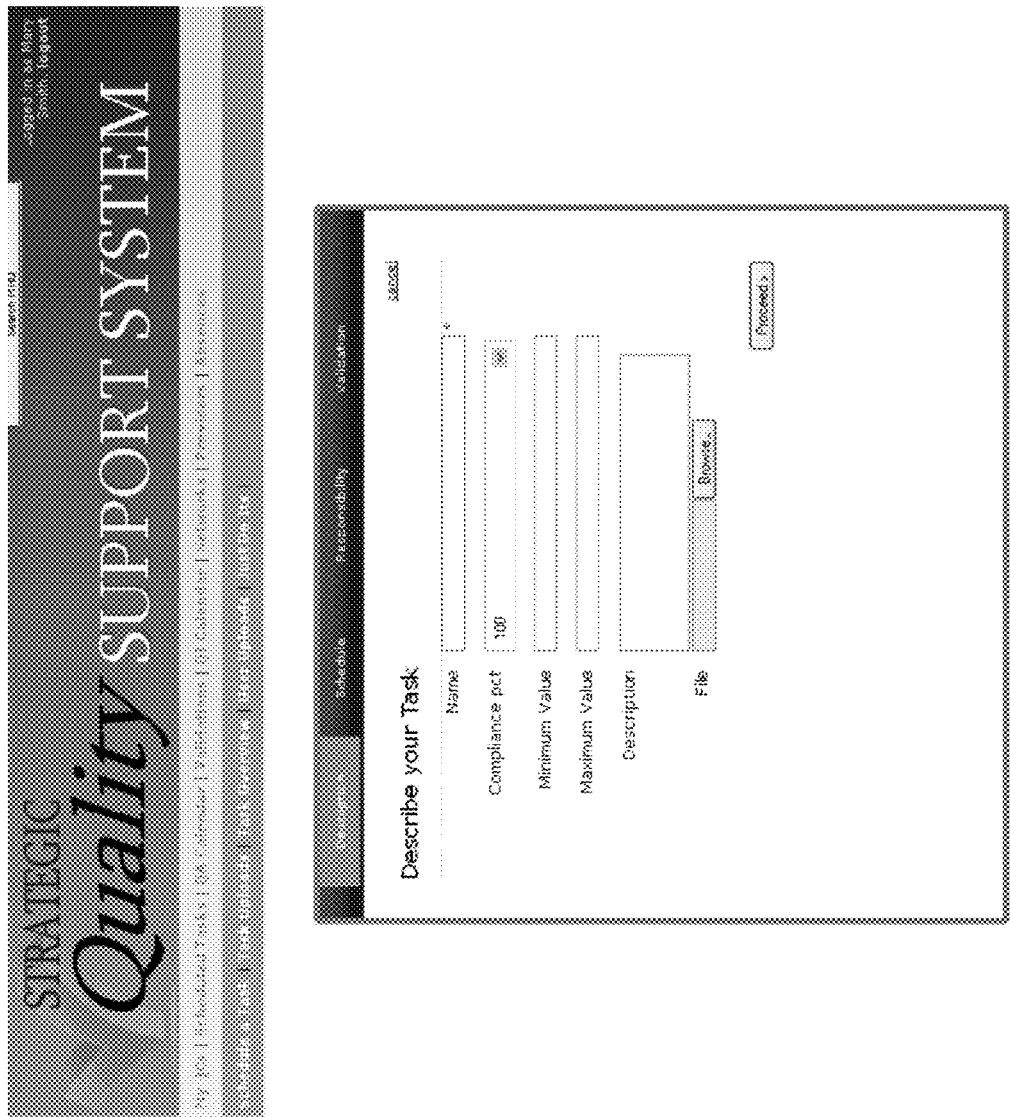
FIG. 19 is a screenshot depicting a task description screen.
Figure 20:
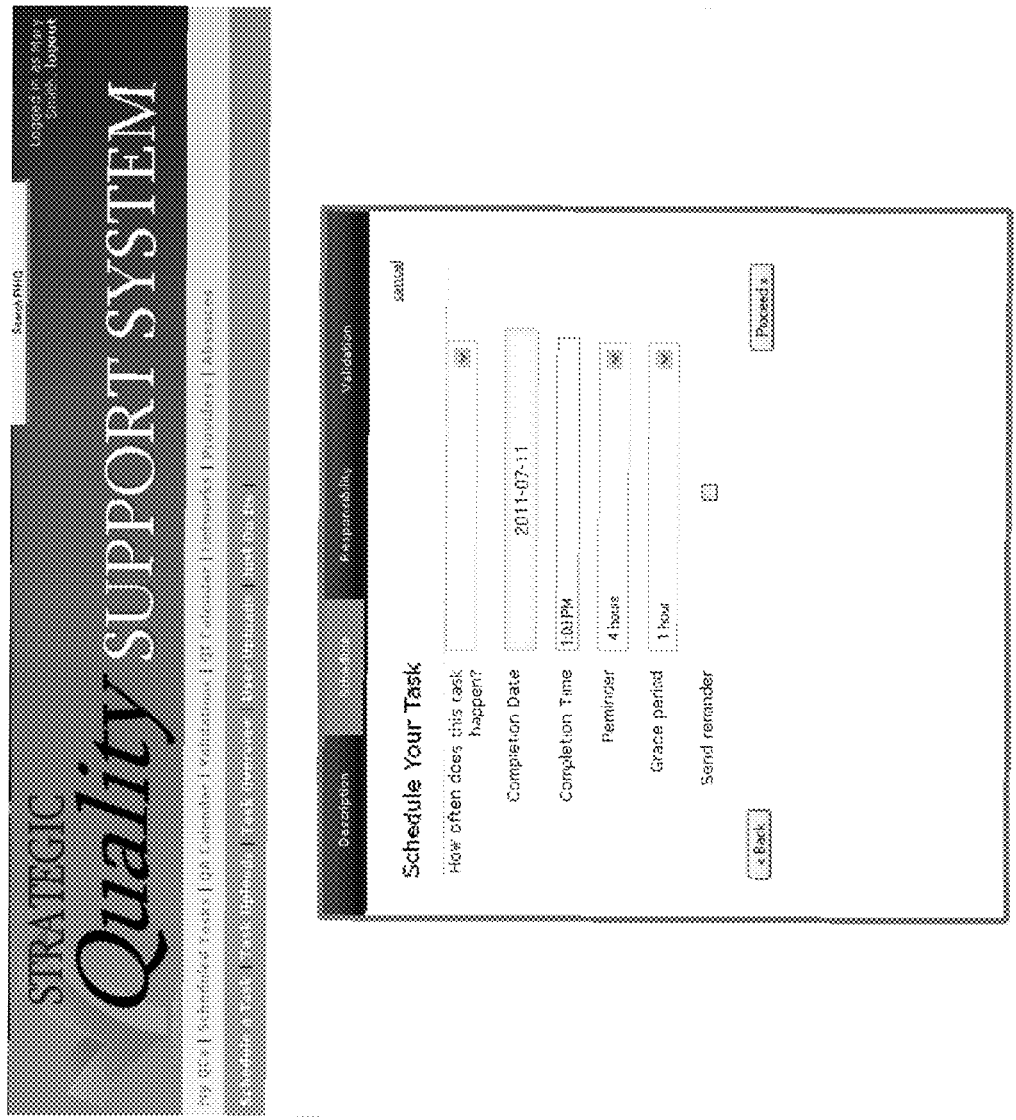
FIG. 20 is a screenshot depicting a task scheduling screen.

The first step in creating a task is to complete the Description screen for the task in the wizard as depicted in FIG. 19. This includes:
 1. Giving the task a name. For example, if a user is creating a task for daily crash cart checks in the emergency department, the name might be Daily Crash Cart Integrity Checks in ED.

2. Selecting the compliance percentage. This is the compliance goal that the user wishes to achieve. For example, activities that are important to patient safety are generally set at 100%.
3. Setting any minimum and maximum numerical values important to defining compliance for the task. If the task has a numerical range for acceptable compliance, such as a required refrigerator temperature, a user can put the minimum and maximum ranges into the System. As people enter values as part of their day-to-day tasks, the System will monitor for compliance within the specified range and will alert users if a value is out of range. For example, if a refrigerator must be maintained between 32 and 40 degrees in order ensure food quality and a value of 44 is entered into the System, the System will not allow the task to be marked compliant and will require documentation of action to address the incorrect value.
4. Entering a description of how the task is completed. This description is intended to be helpful to those people who are responsible for completing the task in the absence of the primary responsible user. As the System allows tasks to have assigned back-up users, this description can be very helpful to the people in those roles.

The description of the task can be entered in two different ways. The description can be typed in the Description box. In this method, it is important to give enough detail that an inexperienced person completing the task has a very high probability of getting it right without additional guidance. If a detailed written procedure already exists, it can be attached to the task by simply browsing and attaching it. This is accomplished by clicking on the browse button to view available files. A user then searches for the file and clicks on it. This will copy it and attach it to the task in SQSS. The user will then see the name of the file and its source appear in the box titled File.

The description feature is designed to save time for those individuals who provide back up for team members. Rather than having to search for instructions or guess how to do the task properly, they can quickly open the description when a back-up responsibility shows up on their "My QCs" list.
5. Once the Description screen is completed, a user would click "Proceed>>" to move on to the screen where the frequency of the task can be set.

The second step in creating a task is to schedule the frequency of the task, as depicted in FIG. 18. This involves:
1. Selecting the frequency for this task. For example, if a task needs to occur every day, a user would select daily. There are a variety of options in the drop-down menu, such as daily, weekly, week days only, monthly and annually, to select from in order to accommodate the wide range of activities in a typical healthcare organization. Depending on the selection made in the drop-down menu titled "How often does this task happen?", a second drop-down menu may open to allow for a more detailed selection. For example, if a user selects daily, a new drop-down box will appear allowing the user to indicate whether it is to be done every 1, 2 or 3 days.
   If a user selects monthly, the choices in the drop-down menu that appears are every 1, 2, 3 or 4 months. The user can then indicate if the activity is to repeat on the same date every month or on the same day of a given week in each month.
2. Selecting the first date that the task will occur for recording and monitoring in SQSS in the box titled "Completion Date." When a user clicks in this box, a calendar will appear to make it easier to select the desired date.
3. Selecting the time of day that the task is to be completed. A user must be careful not to select a time that leaves no margin between the time set in the System for compliance and the time required by an important regulation or safety standard. If used properly, SQSS minimizes the chance that a user will find tasks at risk of being out of compliance with important rules and regulations that can create problems on outside surveys that can affect certifications and payment. If a task is due in the System before it is technically due for the regulators, this allows a user to catch and correct issues in those isolated cases where they may not happen on time in the System. For example, if refrigerator temperatures need to be checked once within a twenty-four hour period between midnight and midnight according to a regulation, scheduling it to be due by 12:00 p.m. leave a twelve hour period to catch the fact that it wasn't done and still make it happen.
4. Selecting the time frame to serve as a "Reminder." The reminder time frame is what determines, when the task will appear on the primary user's "My QCs list." For example, if the task is due at 4:00 pm and it has a reminder of 8 hours, this means the task will appear on the "My QCs list" at 8:00 a.m. The user can get into the System any time between 8:00 a.m. and 4:00 p.m. to complete the task before it runs the risk of becoming late. During this period of time, the task will appear as a "yellow" box on the pixel mapped quality assurance calendar.

The reminder feature is intended to serve as a reminder to a user that a task is due and to create a window of time for a task that is respectful of the dynamic nature of the health care environment but still protects the integrity of the environment. It saves members of the workforce from the need to remember the multitude of compliance activities that continue to grow in the environment. For example, a one month reminder can be used to alert staff to the fact that an important licensing or continuing education requirement is coming due. By setting a one month reminder, the activity will appear on a person's "My QCs" list every day starting one month before the due date. It will appear as "yellow" on the calendar until the time that it reaches the due time on the due date.
5. Selecting the Grace period. The grace period is the amount of time after the scheduled completion time that the responsible user has to record the task in the System before it will be recorded as "Uncomplete" (turns red). For example, if the task is due at 4:00 pm and it has a 1 hour grace period, the task will not be marked "Uncomplete" until after 5:00 pm. The Grace period is designed to be respectful of health care's dynamic nature and gives staff time to get into SQSS to document their activities. The goal is to avoid having documentation responsibilities interfere with meeting the needs of the patients.

It is important when using the System to schedule tasks in a manner that always allows a manager the opportunity to catch an issue and make it right before it becomes impossible to do so. For example, consider a nurse whose professional license renewal is due by Dec. 31, 2011. It would be problematic to make December 31$^{st}$ the due date in SQSS as it gives a manager no time to get the issue addressed before it might impact the staffing schedule if the employee does not take care of it. Thus, in this situation, the due date might be December 8th with a 30 day reminder and a one week grace period. The need to take care of the license renewal would start to show up on the employee's "My QCs" list on November 9th. It would be yellow on the pixel mapped quality assurance calendar from November 9th to December 8th. On that day it would turn orange on the calendar to serve as an alert that the task is late and has the potential to turn red if it is not taken care of in the immediate future. The task would remain orange on the pixel mapped quality assurance calendar until December 15th. If it is not completed by the 15th, it goes red in the System and the System sends e-mail messages to key leaders that a non-compliance exists in the System. Because the non-renewal of the license is not a regulatory and staffing problem until December 31st, the hospital still has two weeks to get it taken care of. This creates a window of time for the issue to be address before it has the potential to create a staffing crisis.
6. Selling an Email Reminder. Email reminders are helpful for those members of the patient care team that do not need to get into the System regularly. To save them the time associated with getting into the System to track their quality responsibilities, SQSS can send them an email reminder that they have a task coming due. This feature is not recommended for Users that have to get into the System regularly because it can overload their mail boxes.
7. When the scheduling for this task is completed, a user would click "Proceed>>" to assign responsibility for this task.

Figure 21:
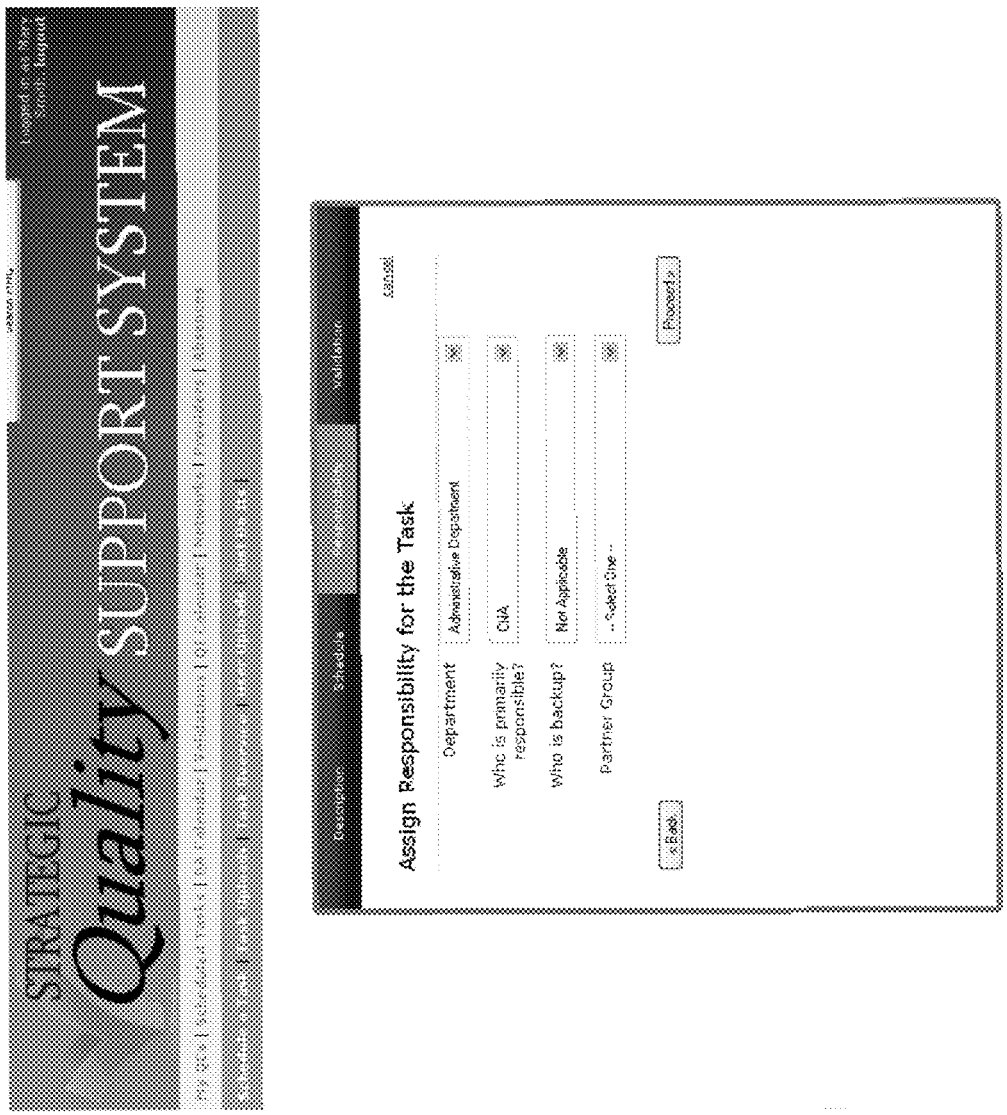
FIG. 21 is a screenshot depicting task responsibility assignment.

The third set of steps in creating a task involves assigning the primary Responsible User and the Back-up User, as depicted in FIG. 21. These steps include:
1. Selecting the department with primary responsibility for the task. For example, if the task is a Daily Crash Cart Integrity Check in the ED, the task would be assigned to the Emergency Department of the nursing division if that is the department determined to be responsible for its completion. This designation is important as it determines which departmental reports the tasks will fall to and which manager is notified when there are compliance concerns.
2. Selecting the user with primary responsibility for the task. Clicking on the drop-down menu will show a list of all users assigned to the selected department in step 1. Tasks can be assigned to a position or a person. For example, if refrigerator temperatures are completed by the aides on duty for the day, the responsible user would be the Task Group of all aides who fill that position and would share that "My QCs" list. As a registered nurse is the only person who can renew his or her license, that task would be assigned to that specific person.
3. Selecting the back-up user that would be responsible for the task when the primary user is absent. Making sure that important compliance activities are done when key personnel are absent has always been a problem for healthcare organizations. The failure to maintain compliance generally occurs because it is not clear what needs to be done during these absences and who should do it. The System allows users to make that assignment as they are building the task. Then, when an individual is marked absent in SQSS, the System identifies all tasks assigned to that individual for the expected period of absence and moves them to the "My QCs" list of the back-up users.
4. Indicating if the task has any Partnering Groups. Health care has a number of tasks that are the regulatory responsibility of one department while another department is responsible for completing them. For example, the operating room has a number of safety standards that are carried out by the maintenance department. While maintenance holds the responsibilities for completion, the manager of the operating room has the responsibility of ensuring compliance in order to protect the patients and staff. It is not enough to simply say that it is maintenance's responsibility or maintenance didn't fulfill its responsibilities.
SQSS facilitates communication between two departments or groups so everyone knows that compliance is good in resource-wise ways. For example, if a task is completed by maintenance, but is an important safety standard for the operating room, maintenance would list the operating room as a partnering group while building the task. Once the task is saved in SQSS, it will show up on both departmental pixel mapping calendars and be linked. When maintenance indicates in the System that the task is done, it turns green on both departmental calendars in order to alert the operating room manager that an important standard has been satisfied. If the task is not done as scheduled, it will show as uncomplete on the calendars of both departments, allowing the operating room manager to proactively act before an error can hurt a patient.
5. When ready to assign validation responsibilities, the user would click "Proceed>>".
6. +

Figure 22:
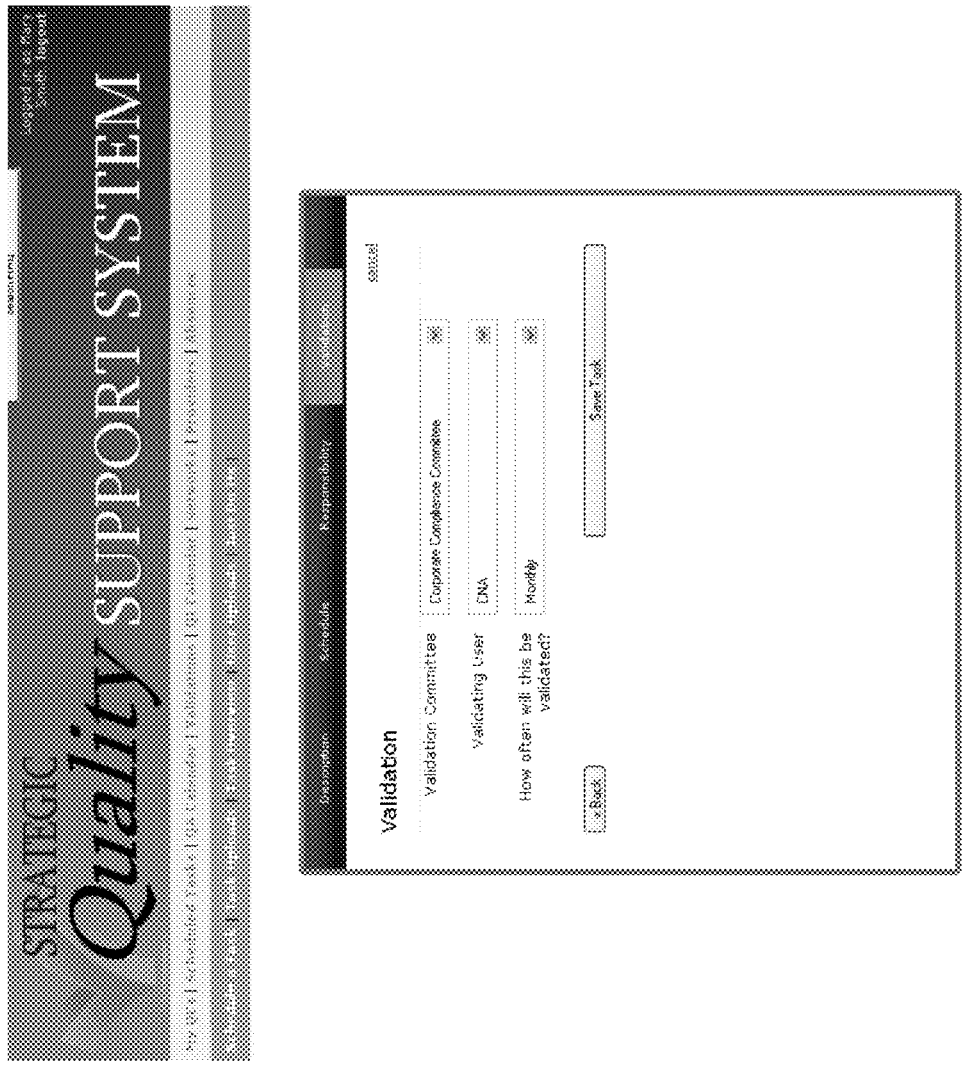
FIG. 22 is a screenshot depicting a validation screen.

Health care is an industry at great risk of quality drift because of its pace and a number of dynamics creating pressures for it. The Validation feature illustrated by way of the screenshot depicted in FIG. 22 helps to guard against this drift and reduce the risk of error by closing the identifying, doing and verifying loop associated with quality management. The steps on this screen of the wizard includes:
1. Selecting which committee has oversight responsibility for the task. Health care has a number of quality-related committees such as infection control, safety, corporate compliance, and utilization review. For some smaller hospitals, these committees are combined but the quality-related function still exists within the committee. The selection of the Validation Committee determines which committee report the information about a task will appear on.
2. Selecting which user is responsible for validation oversight. This is the user that will have responsibility for validating that the task is happening and being done properly. The goal is not to catch people doing something wrong. It is to guard against quality drift in an environment where it is too easy for it to occur. The validator is commonly a member of the designated validation committee. Participating in the validation activities and reporting on them at the committee level helps the committees to fulfill their oversight responsibilities.
3. Selecting the frequency that the responsible validator should validate the task. Frequency of validation is influenced by a number of factors. Some of the most common are the safety critical nature of the task, the risk to patients and staff if quality drift does occur, the history of drift problems in the past and stability of the staff performing the tasks. Choices in the System are monthly, quarterly, bi-annually, yearly and same as task due date.

4. When ready to activate the task in the System, a user would click "Save Task".

A second way to load tasks into the System is by using a customized worksheet that allows multiple tasks to be loaded all at once. This is a time saving feature for tasks that share similarities. For example, consider a hospital that has 282 employees that have to renew professional licenses at different time. Eighty percent of the information needed in the System across these 282 tasks is the same. Using the customized worksheet to load multiple tasks all at once can save substantial time by simply copying the repeatable information to all the tasks. As the smallest of health care's hospitals can have as many as 3000 tasks that can be loaded in this manner and the largest can have as many as 20,000, the time savings is important to freeing people up to meet the needs of patients. To load tasks in mass, a user would:

1. Click on "Task Uploads" in the light green tool bar.
2. Click "Open" in the Download dialog box that appears.
3. Assign a name to the template and save it to prevent the loss of work.
4. Indicate the responsible Department in Column A. The department must appear exactly as it appears in the System. For example, if a department is labeled Nursing Department in the drop-down menus of the Wizard, it must appear on the template the exact same way. Simply typing Nursing will not work. (Required field)
5. Indicate the Task Name in Column B. (Required)
6. Indicate the Compliance Percentage in Column C. This column has a drop-down list of options to select from that match what is in the wizard. The only options that can be uploaded are those in the drop-down list. (Required)
7. Include the Description of the task in Column D. (Optional)
8. Indicate the "minimum numerical compliance value" required for the task in Column E. Optional)
9. Indicate the "maximum numerical compliance range" required for the task in Column F. (Optional)
10. Indicate how often the task needs to occur in Column G. This column has a drop-down list of options to select from that match those in the wizard. The only options that can be uploaded are options from this drop-down list (Required)
11. Indicate the "due date" in Column H. The date entered in this field is the first date that the task should occur to be tracked in SQSS. The date must appear in the following format—"5/1/2011". While it is optional to put a 0 in front of single digit months and days, the year must have four digits—"2011". (Required)
12. Indicate the "due time" in Column I. This is where a user indicates the time that the task should be completed by on the day that the task is due. (The time entered in the Upload Template must use military time.) (Required)
13. Indicate the repeatability cycle for monthly tasks in Column J. If the task occurs on a monthly interval, this field is where a user indicates if the task should reoccur on the same "Date of month" or "Day of week". This column has a drop-down list of options to select from. The only options that can be uploaded are options from this drop-down list. (Required only for Monthly Tasks)
14. Indicate the "reminder period" in column Column K. The time indicated in this field should reflect when the task will first be available for completion by the Responsible User on the "My QCs" list. This column has a dropdown list of options to select from that match those from the wizard. The only options that can be uploaded are options from this dropdown list. (Required)
15. Indicate the "grace period" in Column L. Grace Period: This field defines the window of time that a User has, after the due time, to document the task. The only options that can be uploaded are options from this drop-down list. (Required)
16. Indicate the "primary responsible party in Column M. The e-mail address of the primary responsible user is entered in this field. If the primary responsible user does not have an e-mail address, his or her log-in name is recorded here. If the primary responsible user is a task group, the name of the task group is entered here exactly as it appears in the System. The user account must be created in SQSS before the tasks can be uploaded and assigned to the user. (Required)
17. Indicate if the user is a task group in Column N by selecting Yes from the dropdown box. If the responsible user is a specific person, No should be selected from the dropdown box in this column.
18. Indicate who is the back-up for the task in Column O if the responsible party is unavailable. The e-mail address of the Back-up User is entered in this field. If the Back-up User does not have an e-mail address, his or her log-in name is entered here. The User account must exist in SQSS before the tasks can be uploaded for a selected User. If a task group was entered as the responsible party, a task group cannot be entered as the back-up user. (Required)
19. Indicate if the "back-up user" to an individual responsible party is a task group in Column P. If the primary responsible party is an individual and the back-up user to the individual is a "task group", select Yes from the dropdown box in this column. If the back-up user is a specific person, select No from the dropdown box in this column.
20. Indicate the "validating committee" Column Q. The Committee name must be entered exactly as it appears in the drop-down lists in SQSS. The selection of the validation committee determines which committee report the information about a task will appear on. (Required)
21. Indicate the validating user in Column R. The validating user's e-mail address is entered in this column. If the validating user does not have an e-mail address, the user's log-in name is entered here. The validating user must be different than the primary responsible user and the back-up user. The System will not accept users in these three categories that are the same. The user account must exist in SQSS before the tasks can be uploaded for a selected user. (Required)
22. Indicate how often the validations will occur in Column S. The choice must be entered in the spreadsheet exactly as it appears in the drop-down lists in SQSS. Choices in the System are monthly, quarterly, bi-annually, yearly and same as task due date. (Required)
23. Indicate if a "partnering department" needs access to the task information in Column T. The department name must appear exactly as it does in SQSS. (Optional)
24. Indicate whether the user should receive an "email reminder" in Column U. To have an email reminder automatically sent to the responsible party for the task, a user would type "Yes" in this column. (Optional)
25. Once an upload template is completed, it is uploaded by:
   1. Selecting "User Upload" from the light green toolbar.
   2. Selecting the saved file that contains all the information to be uploaded.
   3. Clicking Upload.

If the file is successfully uploaded, a message will appear at the top of the "My QCs" list indicating a successful upload. If the file has errors in it, a message indicating an unsuccessful upload will appear along with a list of the errors that need to be fixed. The template will not successfully upload any information until all the information is correct. This is to minimize the risk of duplicate information making it into the System.

The Scheduled Task Library

Turning again to FIG. 4 and the Scheduled Tasks Library module 413, the Scheduled Tasks category in the green toolbar contains a library of all the current tasks a facility is monitoring and managing in the Strategic Quality Support System 101. There are several activities that can be performed from this area of the System. From here, it is easy to edit tasks and access logs and history reports related to the different quality-related activities scheduled in the System. This is also where users go to archive tasks that no longer need to be performed but are important to retain for their past history. When one opens the scheduled task screen, as depicted in FIG. 23, the first thing seen is an alphabetized listing of all the tasks in the System.

Figure 23:
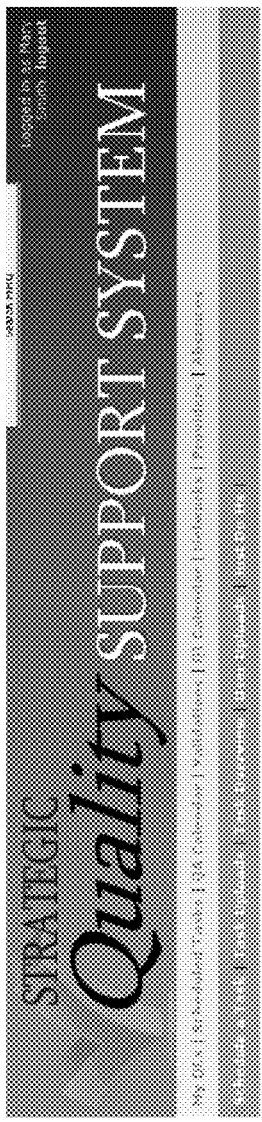
FIG. 23 is a screenshot depicting a scheduled tasks screen.

From the screenshot depicted in FIG. 23, a number of sorting functions can be carried out. The first series of sorts can be accomplished by using fill-in-the-blank and drop-down boxes at the top of the screen. These sorts can focus on the Task Name, the Owner (Primary Responsible User), time frames for the creation of tasks and time frames for the past editing of tasks. It is from this screen that a listing of archived tasks can also be retrieved. There are a number of special notations that are important to know about using these features:

1. It is not necessary to know the exact or complete task name when using the task name feature. Typing any key word in the Task Title box will pull up all tasks that include that key word.
2. Selecting the name of a Task Owner from the drop-down menu will pull up all tasks where that individual is the primary responsible user, a back-up user and the validator.
3. By clicking in the box next to the word Archived and selecting Search, a listing of all archived tasks can be retrieved. By using this feature in any combination with the other sorting features such as Task Name and "date range created", a user can refine his or her search.
4. The Created On and Updated On features are helpful when a user needs to keep track of new tasks or edited tasks for quality control reasons. For example, the quality committee may be responsible for approving all created and edited tasks to ensure that they comply with current standards. Before each monthly meeting a list of all tasks created or edited since the last meeting could be generated to facilitate that process.

Another series of sorts can be accomplished by clicking on the column titles indicated in blue at the top of each column. Sorts include:

1. Name—All tasks are automatically in alphabetical order starting with "A". By clicking on the Name title, the order will shift to a descending order starting with "Z".
2. Department—Clicking on Department will cluster the tasks by department.
3. Owner—Clicking on Owner will cluster the tasks by primary responsible user.
4. Backup—Clicking on Backup will cluster the tasks by back-up user.
5. Validator—Clicking on Validator will cluster the tasks by validating user.
6. Frequency—Clicking on Frequency orders all the tasks in order of most frequently scheduled tasks to least frequently. Clicking on it a second time will reverse the order.

As the number of tasks grows in the System, they will automatically spill over onto subsequent pages. A user can easily move from page to page by clicking Previous or Next at the bottom of the screen. If the desired page number is known, a user can click on that page number. The page that is currently open will always be reflected in black.

The ability to sort tasks in various ways as the number of tasks in the System increase in number becomes increasingly important in expediting access to information. The smallest of health care's hospitals can easily have as many 4,000 tasks in the System while the largest can reach 50,000.

If a task is shared with a Partner Group, it will be repeated at the bottom of the page in the scheduled task library to make it easily distinguishable from all other departmental tasks.

The scheduled task library is also a convenient place to access any instructional or informational pieces that have been attached to a task. They are always located in the Download column and can be accessed by clicking on the blue title of the attachment. Logs, such as temperature and pressure logs, can be accessed by clicking on the word history.

Several pieces of information are available in the history log. There are also a few key functions such as Edit. Achieve and Delete that are possible from this screen. By selecting Edit from this screen, a user can open the Task Editing Wizard to make changes to a Task. This can also be accomplished by clicking on the task name in the scheduled tasks library. Tasks can also be archived from this screen when they no longer need to occur or deleted if that is the appropriate action. Tasks should never be deleted if they contain any history that could be needed at a later date. The deletion function is appropriate for tasks that were created in error or in the event a task was created twice and one needs to be deleted. Otherwise, if the task has any history recorded in the System, it should be archived. When a user selects delete, the System generates a warning and asks if the user is sure that he or she wants to delete the task.

Key compliance values are continuously generating in the System. They include:

1. The percentage of compliance for every task. This means that the task was completed as scheduled and was in compliance with the required standard.
2. The percentage of non-compliance. This means that the task was completed as scheduled but was not in compliance with the required standard.
3. The percentage of uncomplete tasks. This means that the task was scheduled and not done.

Logs for various periods of time can be created by simply indicating the desired start and end dates for the needed report and clicking Filter. When a user clicks inside the boxes, calendars will appear to make it simple to select the desired dates for the sort.

The log portion of the history screen indicates the primary responsible user for the task, the date and time it was completed, the individual who actually completed the task, any minimum and maximum ranges that had previously been set in the System, the value recorded when the task was completed, the status of compliant, non-compliant or uncomplete and any notes that were recorded at the time the task was completed. It is possible to easily view other details about the task by clicking on View in the history log. It is from this screen that a manager can also override the status of a task in the System. This feature allows managers to change the status of activities when appropriate to ensure accuracy of information in the System. For example, an employee completes his tasks but then gets caught up in helping with a patient emergency. He does not have time to get into the System to record his activities before they go Red in the pixel mapping Quality Assurance Calendar. From this screen the manager can override the red and make it green or blue (whichever is appropriate).

The System requires a reason for an override to be recorded. This information is important in the event that the override is questioned at a later date. A task that has been overridden will be reflected as a triangle overlaying a square box on the pixel mapped Quality Assurance Calendar. The triangle is reflective of the original documentation and the box is reflective of the override status. Thus, in the example above, the triangle would be red and the box would be green if the task was determined by the manager to be compliant. The simplest way to remember overrides is that the triangle is the old status and the box is the new status.

Tasks can also be edited from the scheduled tasks library by clicking on the Name of the Task. Clicking on the name of the task will open a task editing screen that is identical to the Task Creation Wizard. Editing a task is as simple as changing the information that needs to be different and clicking save.

Scheduling and Managing Absences

Turning again to FIG. 4 and the Manage Absences module 415, the feature in the Strategic Quality Support System 101 for scheduling absences is designed to overcome one of the most commo reasons that important quality related activities do not occur—the primary person responsible for the activity is absent. Because much of health care is a seven day a week, 24-hour a day industry that never closes, not even for major holidays, it takes a large number of people to manage quality-related activities from day-to-day and moment-to-moment. One important quality-related activity can require several people to provide coverage when one considers variables like vacations, holidays, illnesses and dynamic work schedules that fluctuate based on patient care needs.

As many of the quality assurance activities in health care are safety related and can make a difference between harm and no harm, control of those activities is especially important. Simply skipping them or allowing them to drift away from the level of compliance that fosters reliability can create serious problems for patients and healthcare providers.

The absence scheduling feature in the Strategic Quality Support System 101 is designed for the computer to help in monitoring and managing absences by automatically moving quality-related activities to the My QC List of another trained person when the primary responsible person is absent or for some reason unavailable. When tasks are developed in the System inside the Task Wizard, the primary responsible party is identified along with the individual who will serve as the back-up if that individual is absent.

There are many safety and quality control activities in health care where it is important that they continuously occur as scheduled because of their role in ensuring a reliable and safe patient care experience. These are the activities where people in back-up positions are important. There are others such as license renewal, TB testing and mandatory training that are specific to the individual. In these situations, there is no value in assigning a hack-up. For example, no one can get a nurse's license renewed except the nurse who the license applies to.

It is important to plan for efficiency and effectiveness when assigning people to back-up positions. As health care has traditionally managed these types of activities in a crisis fashion when leaders suddenly become aware of a gap in important safety activities, the ability to plan ahead creates an opportunity to better utilize resources as health care feels the strain of the evolving health care environment. It also fosters the ability to ensure a more reliable patient care environment.

Once the back-up is established, the Strategic Quality Support System 101 will store the information until an absence is recorded in the System for an individual with primary responsibilities for a given activity. When the primary responsible party is absent and activities have been moved to the My QCs list of the back-up individual, the Strategic Quality Support System 101 will provide a banner notice that a user's list contains back-up activities for a team member and the back-up activities will be flagged with the word back-up to the right of the task.

When a user in the System has a planned absence coming up for activities such as off-site meetings, vacations and training, that absence can be recorded as soon as the user becomes aware of it. This is done by clicking on absences in the toolbar. A screen will open where the absence can be recorded in five steps.

1. Selecting the name of the user that will be absent from the user drop menu.
2. Selecting the first date of the planned absence from the calendar that will open up when a user clicks on the box next to First date absent.
3. Selecting the last date of the planned absence from the calendar that will open up when a user clicks on the box next to Last date absent.
4. Recording the reason for the absence in the Description box. This information does not have to be lengthy but can be helpful in evaluating for trends and patterns in illnesses.
5. Clicking on Create Absence, as depicted in the screenshot of FIG. 24.

To edit an existing absence, a user would select absences from the toolbar. A screen will open showing the absences that are recorded in the System for the current month. The Quality Director will see all absences for the organization. Managers will see all absences for those employees who report to him or her.

To delete an absence that is yet to occur, a user would click on the red circle with a minus sign next to the absence to be deleted. Only the System Administrator can impact an absence for a time frame that has already occurred.

To edit an absence, the existing absence first needs to be deleted. Then a new absence can be created.

The System can also generate absenteeism reports by user or for the entire organization. These reports are helpful for employee performance appraisals and meeting regulatory requirements for monitoring trends and patterns in employee illnesses. To generate an absenteeism report, a user would:

1. Select Absences from the toolbar from the yellow toolbar.
2. Select Current Absences.
3. Indicate the date range for the report.
4. If the report is for a specific user, indicate that also. If a specific date range is desired, the user can indicate a Start Date and End Date.
5. Select Filter.

Generating Reports

There are several different reports that are available inside the Strategic Quality Support System. Each of the reports can be filtered down by a specific department, user, committee, and type of task.

History Log

The first report is the task specific history log. This log allows users to view the history of a specific report. The information that is included in this log is as follows:

Dates for each occurrence of this task.

The user that completed the task on each of those dates,

The time the task was completed,

The status of each occurrence,

Any notes that the user entered when completing the task,

Compliance, non-compliance and uncompleted percentages for the specific task, and If there was a minimum and maximum range set for the task, this log will show the range that was set and the number that was entered by the user each time the task was entered.

The history log can be accessed by:
1. Clicking on Scheduled Tasks in the yellow toolbar. This will bring a user to the list of tasks that he or she is affiliated with inside the System.
2. Clicking, on the history link that corresponds to the task that a user needs to view the log for. This will open the log.

The log automatically will show every task occurrence for the last 30 days. However, there is a Start date and End Date box that can be used to filter out specific time frames.

Tasks can be archived from this screen as well. If a task no longer needs to occur but a user wants to keep the information from the task, the information can be stored by:
1. Clicking on the Archive link next to the task name,
2. Clicking OK when asked if the user is sure.

The task will be achieved. This means that the task will no longer show on the My QC lists of the responsible or back-up users but the task will still exist in the Scheduled Task list.

To view all Archived Tasks, a user would:
1. Click on Scheduled Tasks in the yellow toolbar.
2. Select the option box next to Archived.
3. Click Search.

To print the log, a user would:
1. Click on file in your internet browser.
2. Click print.

Figure 25:
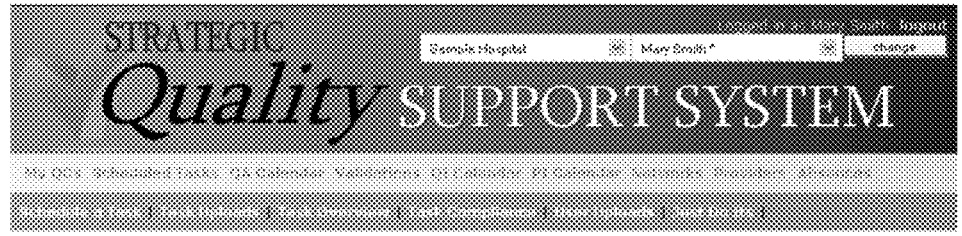
FIG. 25 is a screenshot depicting an example of a pixel mapped quality assurance calendar of the present invention.

Various useful outputs exist in the Strategic Quality Support System 101. FIG. 4 depicts a pixel mapped Quality Assurance Calendar 417 that provides an instant graphical representation of the status of various quality events. The myriad of quality events are color coded based on status (current events, overdue events, uncomplete events, N/A events, compliant events, late compliant events, non-compliant events, late non-compliant events, and future events.) A sample screenshot of the pixel mapped Quality Assurance Calendar can be seen in FIG. 25.

The Pixel mapped Quality Assurance calendar can be converted into a report that can be filtered down by department, committee, user, type of status and type of tasks.

When the pixel view of the calendar is converted to a narrative report, it will list out the information for each task that is shown on the calendar in order of due date and time. The information contained on this report is as follows:

The task name.

Who it was performed by or who is scheduled to perform the task.

The date the task is due.

The current status.

Any notes that were entered for the task occurrence.

The design of the pixel mapped Quality Assurance Calendar facilitates very quick access to information that can target weaknesses that can raise the risk of errors that can harm patients or employees. The volume of information that is generated and must be managed in health care has made it difficult for the industry to be proactive in its efforts to be in control of the patient care environment. This has become especially difficult in the last fifteen years as the rapid growth of technology has rapidly increased the amount of information generated and in need of management. As health care's historical approaches have relied on doing studies after the fact to see if the patient care delivered yielded the desired outcome and if things were happening the way they we supposed to, it never allowed the identification of risks in a timely enough manner to reduce the risk of an error for patients at the time they were receiving care. SQSS makes that information more real-time. It monitors activities for completion and notifies key leaders immediately when something is not done. It then makes it very easy to drill down into the information to identify specific issues that represent opportunities to strengthen the patient care environment.

The pixel mapping Quality Assurance Calendar allows for some of the most immediate access to this type of information. For example, a user can isolate all the red (not completed) tasks with two keystrokes. The user can then convert the pixel map of red boxes to a narrative log with one keystroke. The narrative log can then be sorted by users and type of tasks with less than six keystrokes. The System provides for an activity that has historically taken health care hours to days to complete and allows it to occur in minutes.

To filter down to a specific department, committee, user or task, a user would filter by selecting from one or more of the drop-down menus across the top of the pixel mapped Quality Assurance Calendar screen. These drop down menus populate with organization-specific information put into the System when the facility profile and facility tasks were built. To view only tasks of a specific status, a user would deselect all status options on the legend except the status to be viewed.

The validation report capabilities function exactly the same in the Pixel mapped Quality Assurance Calendar report, except it only shows information about validations that have and need to be completed. The validation calendar can be converted into a report that can be filtered down by committee and user.

This will list out the information for each validation that is shown on the calendar in order of due date and time.

The information contained on this report is as follows:

The name of the Task that needs to be validated.

Who it was performed by or who is scheduled to perform the validation.

The date the validation is due.

The current status.

Any notes that were entered for the validation occurrence.

To filter down to a specific committee or users validations, use the filters on the right hand side of the screen. To view only validations of a specific status deselect all status options on the legend except the status you would like to view.

Using the Task Overview Report

Figure 26:
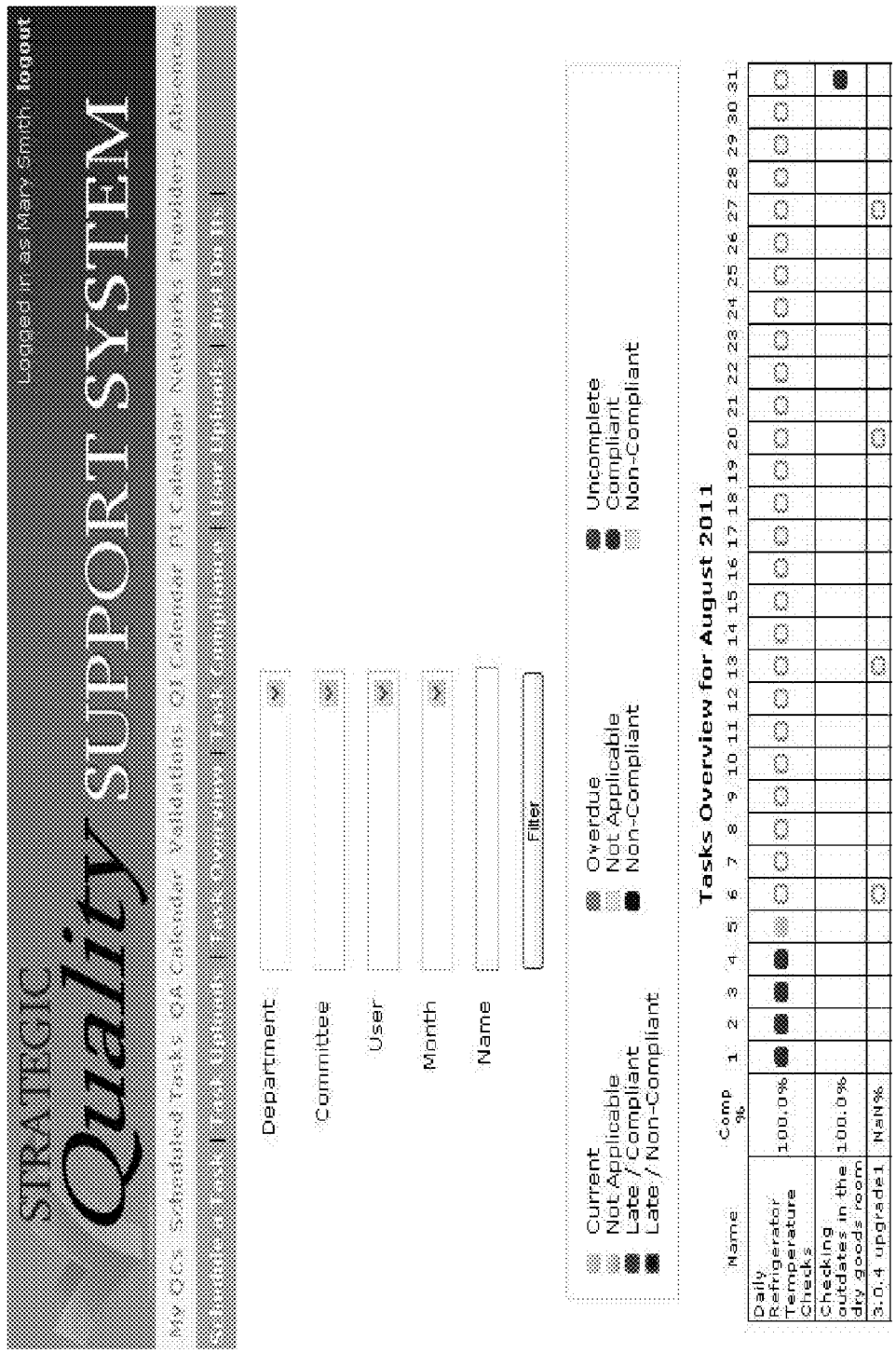
FIG. 26 is a screenshot depicting a task overview screen.

Turning again to FIG. 4, The Task Overview Report 419 allows a user to view the compliance of each task assigned to them during each month. The Task Overview Report 419 is depicted as a screenshot in FIG. 26. This report is a great way for managers to see if there are patterns in non-compliant or uncomplete events or if there are specific tasks that are consistently uncomplete. To view the task overview report, a user would click on Task Overview in the light green toolbar. This report will automatically show any tasks assigned to the requesting department or user during the current month. When managers of departments access this report, they see all tasks for the departments they are responsible for. When individual users access this report, they sec the tasks they are responsible for. The report always shows the current month when it first comes up. Next to each task a user can see a compliance percentage for each task for the selected month. The report will then show each day that the task occurred or will occur during the month and the status of each event. To learn more information about a specific occurrence, click on the colored box for the date you are interested in. The screen that will come up provides the detail information about when the task was due and the people responsible for making it happen.

This report can be filtered down to tasks assigned to a specific department committee, user, or month. If a user is looking for tasks under a specific name, these tasks can be filtered out by typing the task name in the name box. It is from this report that one of three types of user-specific profiles for the purpose of employee performance appraisals can be generated.

Using the Task Compliance Report

Figure 27:
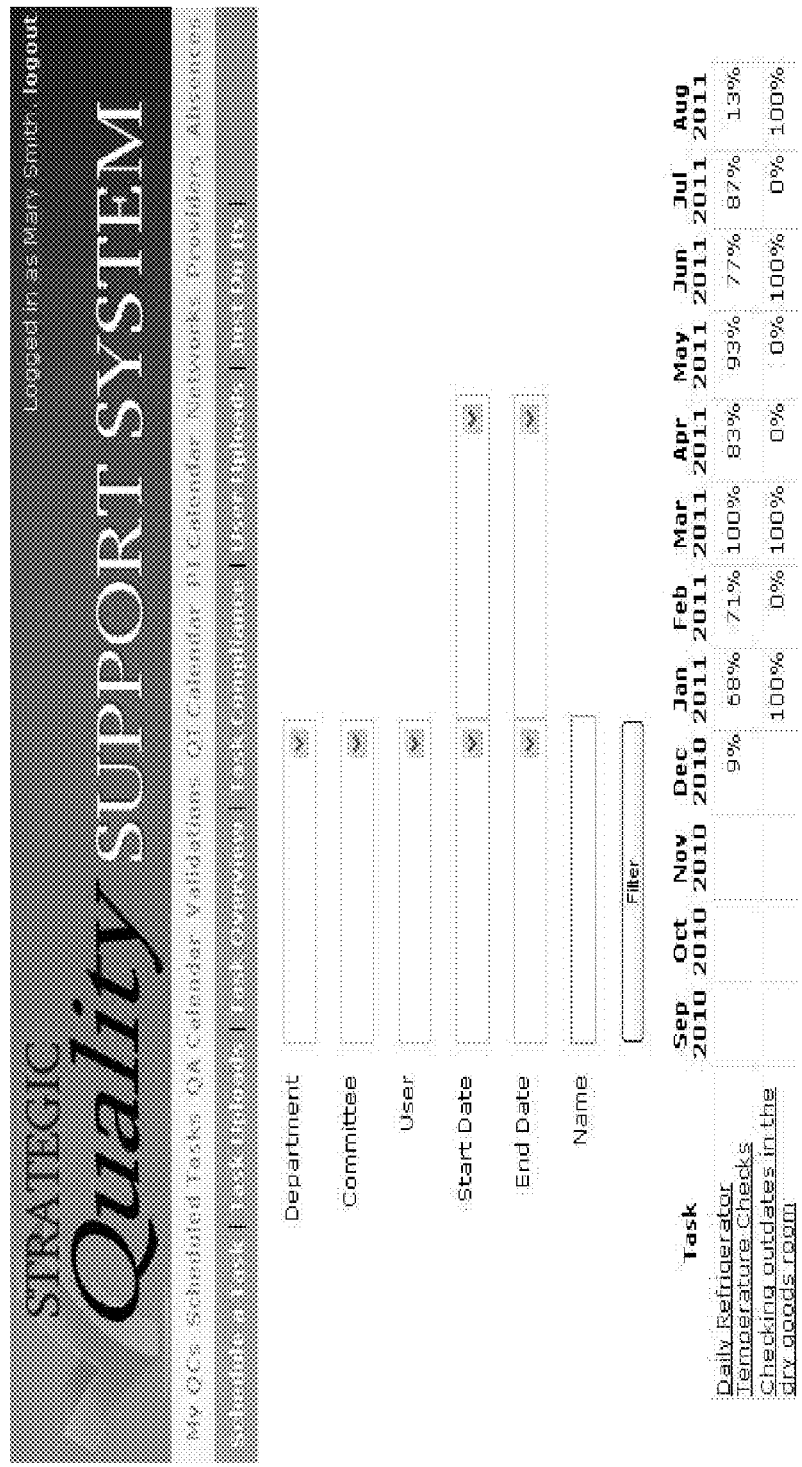
FIG. 27 is a screenshot depicting an exemplary Task Compliance Report.

The Task Compliance Report 421 allows a user to view the compliance of each task displayed in the task overview report over several months. This report depicts if tasks have a consistent compliance percentage over a series of months, if there is a specific area where tasks compliances are consistently low or erratic and if the task compliance is declining as seen with quality drift. To access the Task Compliance Report, a user would click on Task Compliance in the light green toolbar. The task compliance report will automatically show any tasks assigned to the requesting department or user and their compliance percentages for the last twelve months. When managers of departments access this report, they see all tasks for the departments they are responsible for. When individual users access this report, they see the tasks they are responsible for. The report always shows the last twelve months when it first comes up. Alternate timeframes can then be selected by entering the date range desired. A screenshot of an exemplary Task Compliance Report is depicted in FIG. 27. This report can be filtered down by department, committee, user, and start date and end date. If a user is looking for tasks under a specific name, these tasks can be filtered out by typing the task name in the name box. It is from this report that one of three types of user-specific profiles for the purpose of employee performance appraisals can be generated.

The Quality Improvement Calendar

Again referring to the top level diagram of FIG. 4, a Quality Improvement module 433 is depicted.

Figure 28:
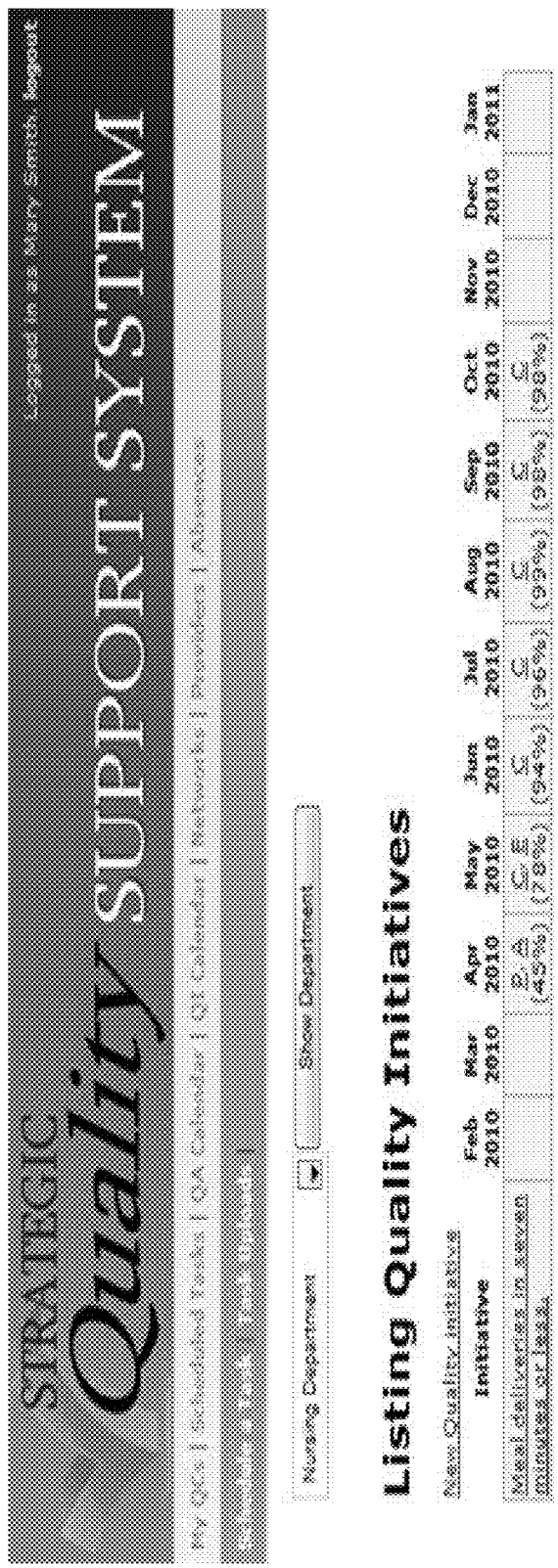
FIG. 28 is a screenshot depicting the Quality Improvement (QI) environment.

Managing a quality improvement initiative in SQSS is relatively easy. The rapid cycle QI calendar is designed to operate as an "at-a-glance" report that helps health care providers to quickly achieve improved performance. By simply looking at the line-up of the letters on the calendar and the shifting of the numerical values that represent progress towards the targeted level of performance, a leader, manager or quality team can quickly access the health of an initiative. By clicking on any of the information in blue, one can review more detailed information. The ability to focus on this information can make it easier to move initiatives along, identify initiatives that aren't strong enough and need enhancements and weed out initiatives that should be abandoned and started again. It creates a better chance of achieving the desired level of performance. The sequencing of the letters demonstrates the health of the initiative, the speed of the improvement and the workforce's movement through the Valley of Despair. The Valley of Despair represents a decline in productivity that always accompanies change. Minimizing this decline in health care is important because it impacts risk for the patients. The greater the decline in productivity and the longer the decline exists, the greater the risk for error in patient care because it forces the staff to have a higher level of competing pressures. The shifting in the numerical values indicates movement toward the target and the speed of the improvement. Together, they distinguish initiatives that are moving along well from those that may need intervention and those where people just need to start over. FIG. 28 depicts a screenshot of the Quality Improvement (QI) environment.

The Quality Improvement Calendar in SQSS supports multiple project management methodologies that reflect the improvement process. They include PACE, PDCA, PDSA, DMAIC and DMAVD. The examples contained herein are presented using PACE. PACE is one that reflects the improvement cycle of Plan, Act, Check and Enhance. The methodology that an organization uses is an individual choice that should be based on what is determined to be the best fit for an organization's culture.

If a user is accessing the System as a quality professional with administrative privileges, he or she will view a drop-down box that allows the selection of the calendar for the different departments in the System. Managers of the different departments will not see this drop-down box as they can only see the quality improvement calendars for their respective departments. If a user has access to the drop-down feature, he or she would select the name of the department he or she wishes to view and click "Show Department".

As improvement initiatives are generally created based on assumptions about cause and effect, it is not unusual to have an occasional initiative that needs to be reinvented—even in organizations that are really good at managing quality improvement. This is an especially strong possibility in industries as dynamic and variable-rich as health care. It is not a weakness to have a bad plan. It can be a weakness to continue to try and repeatedly fix an unhealthy plan. Part of effectively managing a quality improvement initiative is recognizing when to cut one's losses before they become financially, operationally or reputationally hurtful. Starting over with a stronger plan can frequently be more resource and outcome-wise than working to maintain a weak plan with a lot of resource-intensive band-aids.

When analyzing a plan for its general health, there are two critical considerations. The first is its potential to achieve value-adding gain. The second is to do so in resource-wise ways that protect the performance potential of the workforce. These considerations are particularly important for health care as it has a history of investing time in activities that do neither. The industry got comfortable with a type of quality commonly referred to as "soft quality" in the 1980s because it generally worked well in satisfying surveyors but didn't force the industry to challenge status quo. Soft quality involves activities that create the perception of action but rarely lead to value-adding gain. At the same time, it is frequently hard on resources. Education, the creation of policies and procedures, the adding of steps to policies and procedures and the creation of a new form are popular examples of soft quality in health care.

For example, consider a hospital that creates a new form—a very popular form of soft quality in health care that is generally ineffective. The form takes twenty minutes to complete. It must be completed on every inpatient every shift, every day. For every twenty five patients, the impact on the performance potential of the workforce is 4.38 FTEs.

20 minutes×3 shifts×25 patients×365 days in a year 547,500 minutes/60 minutes in an hour 9125 hours/2080 hours per *FTE*

4.38 *FTEs*.

These types of activities are hard on organizations because they deplete discretionary resources and can create unhealthy work environments for people on the frontlines. In the above example, the organizational impact on the performance potential of the workforce is the equivalent of 4.38 FTEs. That means that the workforce's potential to do something else, such as spending time with their patients, was reduced by approximately 4.38 fulltime people.

An important part of managing and monitoring a quality improvement initiative is to maximize outcomes and resource utilization. The sequencing of the letters and the shifting of the numerical values for the quality improvement initiative of "Meal deliveries in seven minutes or less" in FIG. 28 is an example of a healthy quality improvement initiative. Some of the important judgments that can be determined by reviewing this improvement initiative are:

1. The kick-off plan developed appears to have been a pretty healthy one as the initial improvement in a one month period was significant (from 45% to 78%). It has the potential to reduce the amount of time the workforce will spend in the "Valley of Despair".
2. The plan only required two cycles of enhancements to lead to the desired level of performance. It reduced the stress of change on the workforce and minimized the time people spend in the "Ring of Turmoil"—the most labor intensive point in the Valley of Despair.
3. The design of the plan and enhancements for efficiency and user-friendliness made in July and August had supported sustainability as is reflected by the consistently high percentages of compliance reflected from July to October. As indicated in the notes related to those efforts, the enhancements were made to reduce the negative impact of the initiative on performance potential of the workforce. Both enhancements for efficiency saved the workforce time while they also improved the service for the patients.

Observing the sequencing of the letters and the shifting of the numerical values for an initiative, leaders will know where initiatives are. Asking key cause and effect questions about what prompts an initiative to play out the way it does can help to determine how initiatives got to their present levels of performance. Asking additional key questions about how the work-redesign impacts the workforce can determine the potential final impact on the performance potential of the workforce. Recognizing weak plans that cannot lead to the desired outcome or will be too hard on the workforce allows for the timely redirection of efforts. Making timely enhancements that will strengthen the kick-off plan's path to success make it easier for leaders to raise the bar on quality over and above what the original plan was capable of Making additional enhancements directed at fine-tuning user-friendliness and workforce-focused efficiency, leaders can promote sustainability that is resource-wise. If managed more efficiently with the goal of raising the performance potential of the workforce, a leader can raise the bar on quality and productivity simultaneously. The design of the QI calendar facilitates access to the information making the answers to these questions easier to retrieve.

As one gets comfortable in working with the QI Calendars, one will want to set some triggers that will prompt a closer review of different initiatives. This is one of several approaches that can make it easier and faster for leadership to keep initiatives moving and on target. For example a trigger might be a line-up of four Ps. At this point, the concern would be that P has shifted from planning to procrastination. Procrastination occurs for a number of reasons and it is important to identify the cause early so as to intervene. A manager may not know how to proceed and may be afraid to admit it. The manager might be waiting for something else to happen, such as the installation of a new computer, and can't start until it happens. The manager might be stalled by some internal politics that only leadership can address. Whatever the reason, leadership needs to know about it and provide the necessary support to keep the initiative moving.

Another common trigger would be a line-up of C,Es in the calendar. A suggestion would be that the health of a plan is evaluated once a string of four C,Es are achieved. A repetitive cycle of checking and enhancing to strengthen a plan might be indicative of a weak plan. This is commonly seen when a form of soft quality is selected as the plan—education, discipline, the creation of a new form, the writing of a new policy or procedure or the addition of steps to existing policies and procedures. The timely evaluation of a plan to make sure that it will be able to achieve the desired goal without a lot of band-aids is an important aspect of managing an initiative.

Managing a quality improvement initiative continuously is important for its success. One of health care's greatest mistakes over the past three decades has been to treat quality improvement as an episodic activity that occurs once there is a known problem or in preparation for an upcoming survey. Effective quality improvement works to be out in front of the issues that can create risk for patients and providers. Its purpose is to proactively secure a more successful future for an organization given what knowledge and resources are available at the time. It is about the business of remaining competitive and protecting the financial, operational and reputational health of an organization. There are three basic types of improvement initiatives, all of which can be managed in SQSS:

1. Those where the opportunity to improve is clear because an issue, such as an incident or a near miss, has introduced or raised awareness of a risk or a less than desirable state.
2. Those where risk is always present or can easily increase because of the nature of the patient care situation. The presence of constantly shifting variables that can influence the risk makes it important to continuously monitor and manage the environment. Changes must generally come periodically in order to maintain control of the environment. Thus, there is never a time when the initiative would come to an end. Preventing medication errors and healthcare associated infections are examples of these types of initiatives.
3. Those where improvement is necessary in order to keep pace with the constantly evolving health care environment.

Figure 29:
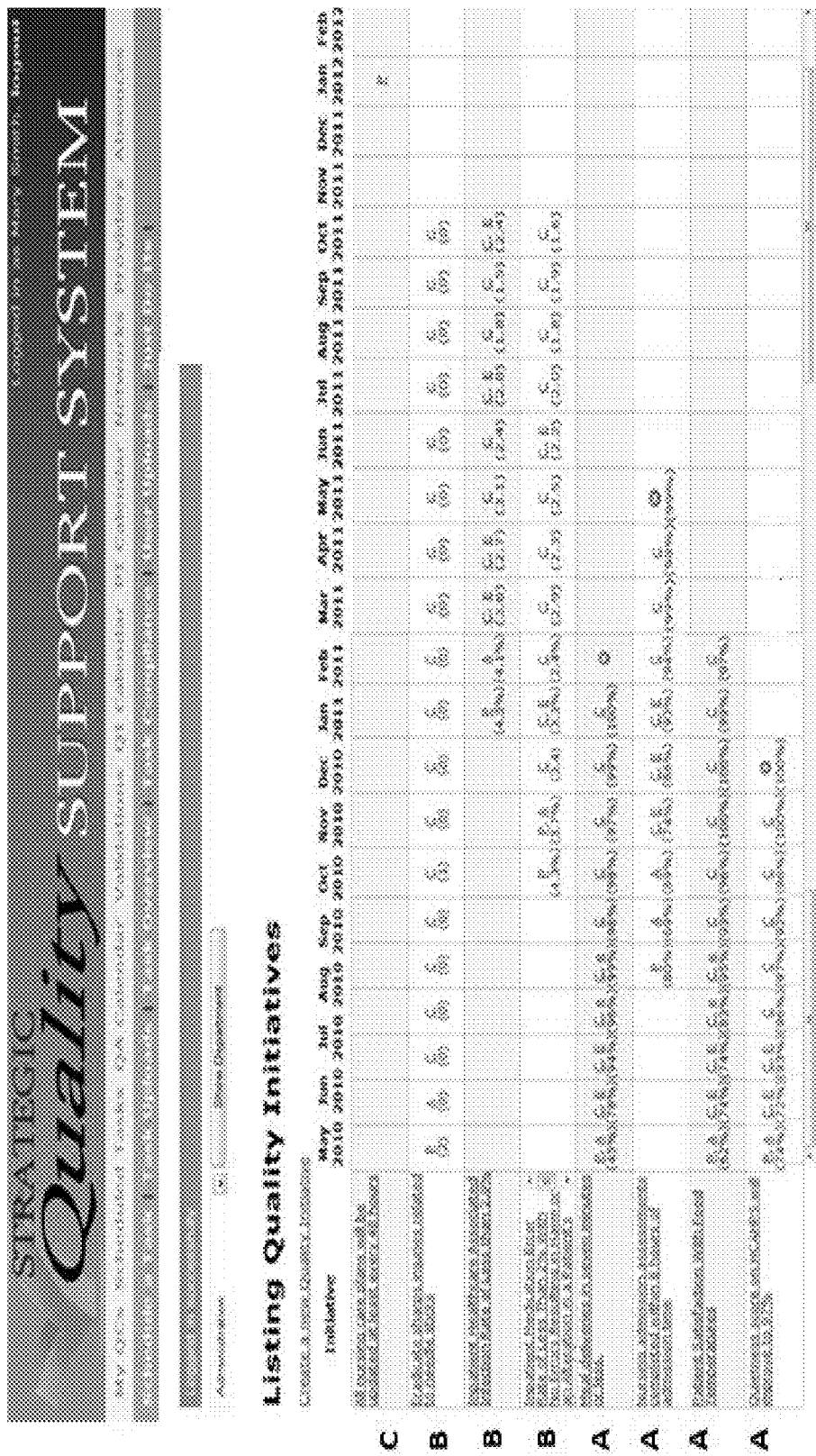
FIG. 29 is a screenshot depicting all three types of improvement initiatives.

All three types of improvement initiatives are reflected in the screenshot of FIG. 29. Meal deliveries in seven minutes or less, improving patient satisfaction with food temperatures, raising the quietness score on the HCAHPS surveys to greater than 90%, and improving the timeliness of the admission assessment (all marked with A) are examples of initiatives where the level of performance is less than desirable. Each has the potential to negatively influence the patient experience if not improved and thus negatively influence the patient/provider relationship. Improvement is directed at taking performance to a more desirable level.

The eradication of sharps injuries related to needle sticks, the occurrence of healthcare associated infections at a rate of less than 2% and the occurrence of medication errors at a rate of less than 2% with no errors resulting in harm or an alteration in a patient's plan of care (all marked with B) are examples of activities that started out as initiatives to take the level of performance to a more desirable state and then remained active because of their impact on safety and vulnerability to even minor shifting of variables. They all have significant safety implications where the occurrence of just one error can have a high potential of permanent and/or devastating harm. They also have a high risk of reoccurrence as they are impacted by so many variables, many of which are constantly shifting. Even after achieving the target level of performance, long term close monitoring is advisable because of the case with which risk can increase and quality drift can occur. For example, new medications are constantly being introduced and many have much riskier consequences if administered in error or in combination with some other medications. Many of these risks are not known when the medication is first introduced into the market. The continual monitoring of error rates increases the likelihood of catching a significant risk before it can escalate too far. Healthcare acquired infections are probably health care's best example of a serious risk where the variables are constantly realigning and shifting. Catching and understanding the alignment of those variables that allow a patient to develop an infection early can have a significant impact on reducing the risk of harm. For example, a hospitals infection rate may start to creep up. Timely investigation reveals that a new surgeon and three other employees hired have less than optimal practices for minimizing the risk of introducing bacteria that can cause infection into their patient care practices. Very timely intervention can reduce the risk for the patients.

Ensuring that nursing plans of care are updated at least every forty-eight hours (marked with a C) is an example of an initiative created to keep pace with an evolving market. As the length of a typical hospitalization has gotten shorter and the pace of care has become faster and more dynamic, timeliness has become an increasingly important attribute of any health care activity.

Monitoring and managing all three types of improvement initiatives in one place such as the SQSS QI Calendar makes it easier and faster for leaders to "have the bubble". While the workforce is the instrument of change, leaders are the agents of change. Quickly knowing the state of the multitude of quality initiatives that can be playing out simultaneously and acting to support them towards their intended targets distinguishes those who have the potential to keep pace with a very dynamic and demanding environment and those who risk failure.

Once an initiative is created, it is time to start managing it. The responsible party for the initiative will document the state of progress each month. The monthly documentation encourages initiatives to keep moving and allows key leaders of quality such as the quality committee to track them and determine in a very timely manner when support is necessary.

Most departments do not formally report on quality improvement more than quarterly but the System makes that information immediately available at all times to the quality professionals responsible for ongoing monitoring. As data does not normally shift fast enough, monthly reporting is generally not a good use of people's time. The one exception to this involves safety critical activities where very timely action and movement is important to protecting human life. Even though a department manager may only formally report quarterly, it is still important for someone, such as the quality director, to track movement from month to month to help maintain the focus on the initiatives with the goal of timely action. The manager provides the day-to-day management of the initiative. This individual with administrative responsibilities provides timely oversight for real-time intervention while the responsible quality committee provides monitoring and management from the big picture point of view—a strategic focus.

The dynamics and stresses of the current healthcare environment make it easy for people to lose focus. Weeks or months can easily pass without action if there is not some formal mechanism for accountability as is provided by the QI calendar in SQSS. This is generally not because of purposeful neglect, but because of the dynamics of the environment. While the delay may not seem like a big deal, every passing month represents a potential lost opportunity and an infringement on resources. Delays during critical times of an initiative such as the period when initiatives are being enhanced to achieve a target can be very hard on the workforce because of the time they spend in the "Valley of Despair".

Creating an Initiative

To create a quality improvement initiative, the first step is to select the project management methodology that is used by a user's organization. There are several advocated in different literature. Rather than dictating one in the System, SQSS supports the five more common ones as the ideal for an organization is to select the one that is the best cultural fit. To select the project management methodology, an administrative user would:
1. Select Providers from the yellow toolbar.
2. Click on Edit next to the name of the organization. This step is only necessary for administrative users who have access to more than one facility in the System.
3. Select the methodology used by the organization from the drop-down list next to the words "Improvement plan." The options include:
   PACE—Plan, Act, Check and Enhance
   PDCA—Plan. Do, Check, and Act
   PDSA—Plan, Do, Study and Act
   DMAIC—Define, Measure, Analyze, Improve and Control
   DMAVD—Define, Measure, Analyze, Design and Verify
4. Click Update Provider at the bottom of the screen.

Once the project management methodology is selected, the first improvement initiative can be built. The selection of the methodology only has to occur once when first getting started in the QI feature. To create a quality improvement initiative, a user would:
1. Select QI Calendar from the yellow toolbar. For an administrative user, a drop down box will be the first thing to appear to select the departmental QI calendar that the initiative is to apply to. For department managers, the System will take them directly to their respective calendar. A departmental manager cannot see any calendars except those he or she is listed as manager for.
2. Select Create a New Quality Improvement Initiative.
3. Fill in the blanks on the screen that will open. These steps include:
   a. Selecting a Name for the initiative being created.
   b. Selecting a Label for a value that will be manually entered into the System if a user will not be entering a numerator and denominator. SQSS is designed to automatically calculate the percentage reflected on the calendar if a numerator and denominator is entered. The label field is for values that are already calculated in another system or for raw numbers that need to be entered. For example, a patient satisfaction value from a separate system may be the value that the initiative is working to impact. Rather than entering the numerator and denominator that are used to calculate the value in the other system, the label field allows a user to simply add the final value.
  c. Creating a Label for the numerator to be entered into the System if step b is not the approach.
  d. Creating a Label for the demoninator to be entered into the System if step b is not the approach.
  e. Indicating the Target value a user is striving to achieve with the initiative. This value will be reflected as a line on the graphical reports generated by the System to measure for success.
  f. Providing a brief description of why the intiative is important to the organization's future and how it will raise the bar on the product or service provided to the public. The description is important in evaluating an initiative over time to make sure it is not drifting away from its original goal and during the initial approval activities of new initiatives to ensure that they are not types of soft quality.
  g. Selecting "Create Quality Initiative."

Adding an Entry to an Initiative

Adding an entry to an initiative is accomplished through a wizard where the information is entered. To do this, a user:
  1. Hovers over box for the month where the entry is to be made. A "Green Circle with a plus sign (⊚) will appear.
  2. Clicks on the circle and a wizard will appear for creating a "New Quality Initiative Stage."

Once a user is in the wizard, it is a matter of filling in the requested information. This involves:
  1. Recording the numerical information that indicates the current state of performance.
     Sometimes this will be as simple as recording a value such as the number of sharp injuries from a needle stick. In other initiatives, it may involve recording a numerator and denominator such as the number of inpatients who develop a healthcare associated infection and the total number of inpatients. When numerators and denominators are recorded, the System will automatically calculate and record the percentage on the calendar. Which type of value(s) is recorded is determined when the initiative is created.
  2. Indicating the type of improvement process activity that was engaged in during the month: creation of a plan created, acting to implement a plan, checking a plan for impact in creating the desired improvement, enhancing a plan to strengthen its potential of leading to the desired outcome, enhancing a plan to make it more efficient and user-friendly to the staff, or stopping a plan and placing it in hiatus because it had achieved its target level of performance and it was determined that habit conversion had occurred.

It is generally suggested that it takes people an average of six months to incorporate a new behavior as a permanent habit. The time is dependent on a number of factors such as fatigue, stress, competing priorities, the size of the change and whether the desired behavior is easier or harder to perform than the old way. Once the desired level of performance is achieved, it is advisable to continue to monitor an initiative for approximately six months. It is during this time that leadership is working to make the activity more efficient and effective for the workforce and people are able to incorporate the new behavior as a day-to-day habit. A great role for the quality committee is to monitor for the right time to stop an initiative.

An important conversation when stopping an initiative relates to what activities will be necessary to help maintain the achieved level of performance and create the red-flags that let a user know that quality drift is occurring. Health care is an industry where the risk of quality drift runs high. It is not a factor of good versus bad people as much as it is about an environment where the stresses and competing priorities run high enough that it is easy for performance to slowly and insidiously drift in a negative direction. One of the primary purposes of quality assurance activities, commonly referred to as quality control activities, is to reduce the risk of such drift. The design of an effective work environment is one that helps the workforce be consistent with new behaviors in efficient and resource wise ways. Some examples of these types of reminders, triggers and flags are the creation of a QC to prompt the task to occur, the creation of a simple reminder QC to prompt people to think about an important safety behavior periodically or to include an activity as a point of review on one of the worksheets in the SQSS.

3. Including any pertinent notes that describe the findings and activities that occurred during the reporting month. These might include things like changes or enhancements that were made, why they were made, significant experiences since the plan was initiated, and additional findings. If an activity is parked for initiation at a later date, the reasons why it is being parked and any interim precautions being taken to protect patients and staff should be documented.

Parking a QI Initiative

It may be necessary to occasionally delay the start of an improvement initiative because of other activities that are going on. Overloading people and negatively impacting their productivity too greatly is generally detrimental to the potential of success. Parking is commonly done so that an initiative doesn't get lost but its implementation can be delayed until a department has closed out other initiatives it is working on or until the right conditions are available to complete the initiative. It is generally done when an initiative is not safety critical and can be delayed without negatively impacting patient care delivery, safety or the financial, operational and reputational health of an organization. For example, a clinic might decide to put in a new handicapped accessible ramp. Doing this in January would be a problem for areas where snow and cold temperatures make outside work a problem. Putting it on maintenance's calendar and parking it until early summer makes sure that it is not overlooked and facilitates long term planning. It let's everyone know that this is recognized as an important activity and is in the cue.

To park an initiative, a user will:
  1. Determine the month in which he or she wants the responsible party to begin the planning process—where the initiative will be parked.
  2. Hover over box for the month where the initiative is to be parked. A "Green Circle with a plus sign" (⊚) will appear.
  3. Click on the circle and a wizard will appear for creating a "New Quality Initiative Stage."
  4. Select "P" for planning.
  5. Document the reason for parking the initiative.
  6. Click "Create QI Period".

Editing and/or Deleting an Entry

Occasionally, an entry in the QI calendar will need to be edited or deleted. Some of the more common reasons are that there is an error made in creating the entry or an entry is made but assigned to the wrong initiative. To do this, a user:
  1. Clicks on the blue phrase or letter in need of editing.
  2. Select Edit or Delete as is appropriate to the action the user wishes to take.
  3. The wizard for "Updating a Quality Initiative Stage" will open with all the current information. The user can make the necessary corrections and close the wizard.

Creating a QI Report

There are a number of reasons why a user would want to create a quality improvement report. Many healthcare committees have oversight responsibilities that can require reports and leadership teams use reports to help them make decisions about future planning. The QI report features allow users to create multiple combinations of reports for a variety of reasons.

To create a report, a user:
1. Selects QI calendar from the yellow toolbar.
2. Clicks "QI Reports".
3. Clicks "Create New QI Report".
4. Creates a Name for the new QI report.
5. Selects all the QI initiatives from the drop-down list titled Select Options.
6. Clicks "Save Report".

To review an existing report, a user:
1. Selects QI calendar from the yellow toolbar.
2. Clicks "QI Reports".
3. Clicks on the name of the report wanted for review.

To edit an existing report, a user:
1. Selects QI calendar from the yellow toolbar.
2. Clicks "QI Reports".
3. Clicks on name of report requiring editing.
4. Clicks "Edit".
5. Deselects and selects changes.
6. Clicks "Save Report".

Performance Improvement Calendar

The third module of the Strategic Quality Support System 101 is a Performance Improvement module 435, as depicted in FIG. 4.

A performance improvement initiative consists of a number of quality improvement initiatives from different departments and professional groups that come together to achieve some larger goal. The different quality improvement initiatives are managed in the respective quality improvement calendars and brought together in the performance improvement calendar to facilitate monitoring and management. The first step in establishing a performance improvement initiative is to determine the performance improvement goals.

The Strategic Quality Support System allows for the identification of two goals per initiative—a patient-focused goal and an operational improvement goal. The patient-focused goal identifies the improvement that will be achieved in patient-focused perceptions or outcomes (such as satisfaction or the reduction of a complication rate). The operational improvement goal reflects the actual change in operational performance that will lead to change in patient perceptions.

Not all performance improvement initiatives will have two goals. While many are established to impact a specific patient perception or outcome, some are directed at keeping pace with a highly dynamic market or addressing some issue that can have negative financial, operational and/or reputational consequences it left as is. As one of the most important business goals of any service organization is to create satisfied customers and secure patient loyalty, it is advisable to always consider how a performance improvement initiative can influence patient perception.

The next step once the performance improvement goals are established is to determine the quality contributions from the different departments and professional groups that will be necessary to achieve the larger goal. Building a healthy performance improvement initiative is an activity where leaders back out of the larger goal to determine all contributions necessary to make it happen.

One of the most common mistakes in establishing a performance improvement initiative is to leave key contributors out of the initial effort. This occurs for many reasons, but some of the most common are related to the desire to avoid conflict and organizational politics. While these choices seem to make the initiative easier in the beginning, they generally tend to slow initiatives down, force them to plateau well below their potential and foster feelings of animosity that eventually foster an even bigger conflict at some later point in time. Healthy change management recognizes that conflict is generally part of change management. How it is handled and managed determines whether it will become healthy or unhealthy in the change management process.

Like all other sections of the Strategic Quality Support System, a performance improvement initiative may be created through a series of wizards. The wizard allows a user to establish the patient-focused and operational improvement goals for the initiatives. A healthy performance goal identifies what is to be improved and the target level of performance for it. For example, "95% of all emergency room patients will rate the turn-around time in the emergency room as a 5". To establish these goals, a user:
1. Selects PI Calendar from the yellow toolbar.
2. Select "New PI Initiative". A wizard will open where the patient-focused goal and the operational improvement goal that will lead to the patient-focused goal associated with the new performance improvement initiative can be entered.
3. Create a name for the initiative.
4. Select the name of the team leader for the initiative from the drop-down menu. 5. Identify the patient-focused goal and operational improvement goal for the initiative.

Not all performance improvement initiatives will have two goals. As discussed above, some will only have an operational goal as they are directed at keeping pace with the evolving patient environment. Those with patient-focused goals will always have an associated operational improvement goal.

Figure 32:
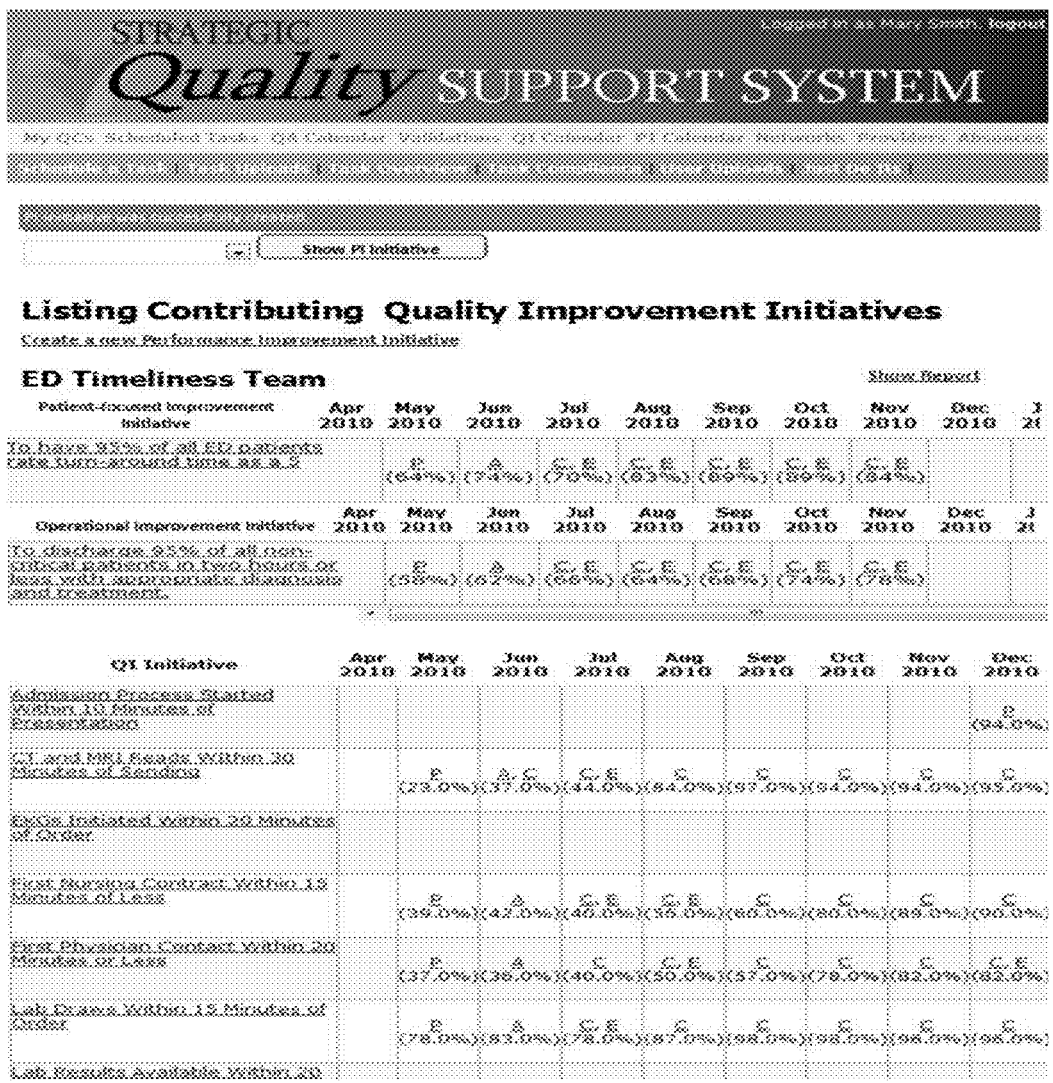
FIG. 32 is a screenshot depicting quality and performance improvement initiatives with percent completion information.

To establish the patient-focused goal and the operational improvement goal, a user would:
1. Select a Name for the patient-focused goal wanted. The name should reflect what a group is working to achieve.
2. Select a Label for the patient perception or outcome that will be manually entered into the System if a user will not be entering a numerator and denominator. The Strategic Quality Support System will automatically calculate the percentage reflected on the calendar if a numerator and denominator is entered. The label field is for values that are already calculated in another system or for raw numbers that need to be entered. For example, a patient satisfaction value from a separate system may be the value that the initiative is working to impact. Rather than entering the numerator and denominator that are used to calculate the value in the other system, the label field allows you to simply add the value, as depicted in FIG. 32.
3. Create a Label for the numerator to be entered into the System if step 2 is not the approach. See FIG. 30.
4. Create a Label for the demoninator to be entered into the System if step 2 is not the approach. See FIG. 30.
5. Indicate the Target value that the group is striving to achieve with the initiative. This value will be reflected as a line on the graphical reports generated by the System to measure for success.
6. Select a Name for the operational improvement initiative that is important to the larger performance improvement goal. The name should reflect the operational improvement the group is working to achieve.

7. Select a Label for a value that will be manually entered into the System if a numerator and denominator will not be entered
8. Create a Label for the numerator to be entered into the System if step 7 is not the approach.
9. Create a Label for the demoninator to be entered into the System if step 7 is not the approach.
10. Indicate the Target value that the group is striving to achieve with the operational improvement. This value will be reflected as a line on the graphical reports generated by the System to measure for success.
11. Select the quality improvement initiatives that are contributors to the larger patient-focused and operational improvement goals for the drop-down menu that lists all the quality improvement initiatives in the System. If a necessary quality improvement initiative is not available in the list, it will need to be added to the appropriate QI calendar.
12. Select "Create Performance initiative."

If the initiative is successfully created, a message will appear in a bar indicating that a "PI initiative was successfully created." If there is a problem with the initiative because a required field is incomplete, a message indicating the error will appear. The names of the patient-focused (if created) and the operational improvement initiatives will also appear in the applicable fields, as seen in FIG. 31.

The design of the performance improvement calendar in the Strategic Quality Support System makes managing complex initiatives relatively easy. The performance improvement (PI) calendar is designed to operate as an "at-a-glance" report and generate easy to create and view graphical reports. It pulls all the contributing quality improvement initiatives into one report to make it easier to know who is making progress, who is not making progress, and where interventions may be necessary. By simply looking at the line-up of the letters on the calendar and the shifting of the numerical values across the different contributing initiatives, a leader, manager or quality team can quickly access the health of an initiative. By clicking on any of the colored information areas, one can review more detailed information. The ability to focus on this information can make it easier to move initiatives along. It creates a better chance of delivering the desired level of performance and keeping individual improvement contributions from going astray.

As demonstrated in FIG. 32, leaders and team members can see the status of each performance improvement goal and each departmental or professional group contribution at-a-glance. As the individual contributing groups are updating their quality improvement initiatives in their respective QI calendars, the applicable PI calendar is updating. The only numbers that may need to be manually entered are those for the two PI goals if they come from different sources.

Some contributing groups may not have active quality improvement initiatives when the PI initiative is initiated. For example, in FIG. 32, the Admission's Department did not initiate a quality improvement initiative until December of 2010 while many of the other departments had started their initiatives in May of 2010. The Admission's Department was able to meet its targeted contribution of starting the admission's process within ten minutes of patient arrival until December. In December, the department experienced a significant change in personnel as two key, long term employees resigned. Staffing holes and the orientation of new people made meeting the target problematic and prompted the department to initiate a quality improvement initiative. Rather than simply allowing the staffing crisis to be an excuse that justified the decline in performance, the department had a goal of re-achieving the targeted level of performance as quickly as possible so as not to negatively impact the ground gained in the larger initiative. Similarly, during the duration of the time reflected in FIG. 32, EKGs were initiated within 20 minutes of the physician order. In March of 2011 (a time not reflected in FIG. 32), the Department needed to initiate a quality improvement initiative due to an increase in volume that prompted the current staffing and scheduling configurations to no longer meet the demand.

As performance improvement initiatives are frequently directed at improvement of one or more of the five critical business outcomes—1) patient satisfaction that promotes patient loyalty, 2) new patient acquisition, 3) patient retention, 4) profitability and 5) market domination, it is not unusual for contributing quality improvement initiatives to start up, go into hiatus and then reactivate when shifting variables make it impossible to continue to hold the desired level of performance. An increase in volume and a significant change in personnel or processes are the most common reasons for a decline in performance. It is not necessarily reflective of a negative. It is generally the result of a realignment of key variables. It only becomes a negative when it goes unaddressed and has a detrimental impact on one or more of the five critical business outcomes. The quick identification of the need to reactivate an initiative to reestablish a desired level of performance is one of the ways healthcare providers maintain the reliability of the patient experience that promotes loyalty and secures the financial, operational and reputational health of the organization.

Figure 33:
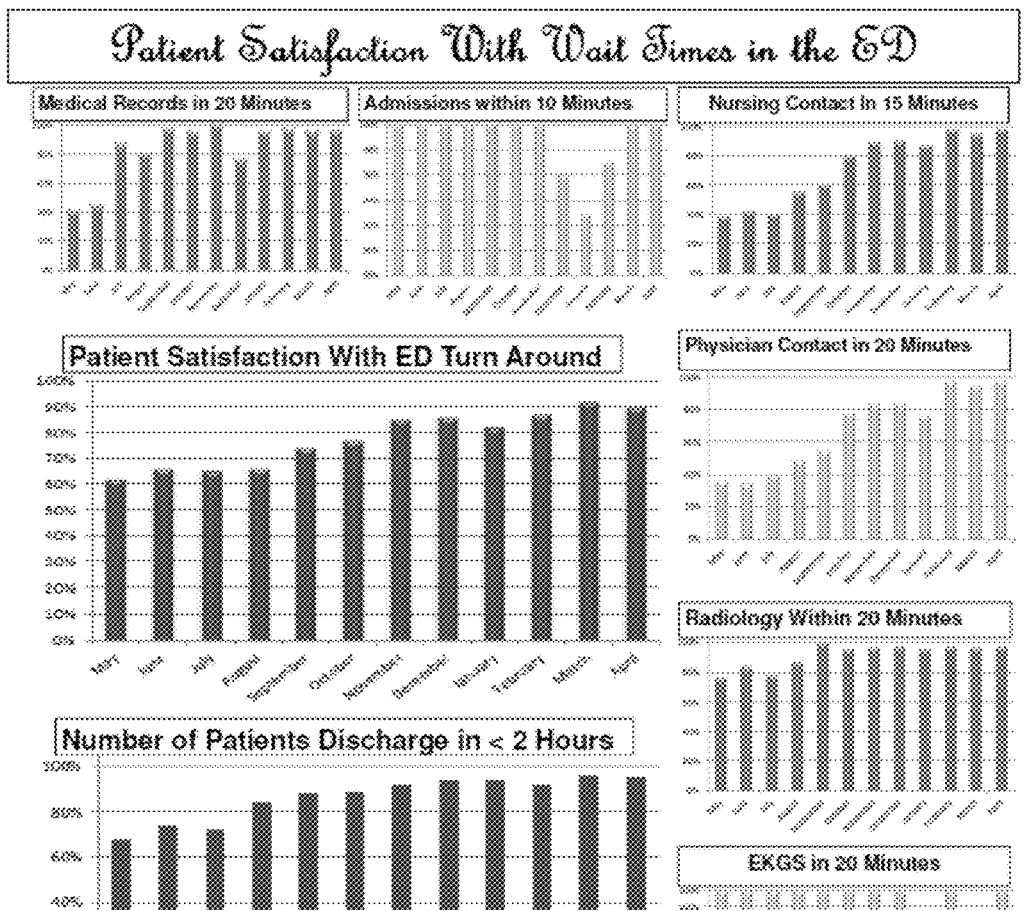
FIG. 33 is a screenshot of part one of a graphical scorecard to track the progress of performance improvement initiatives.
Figure 34:
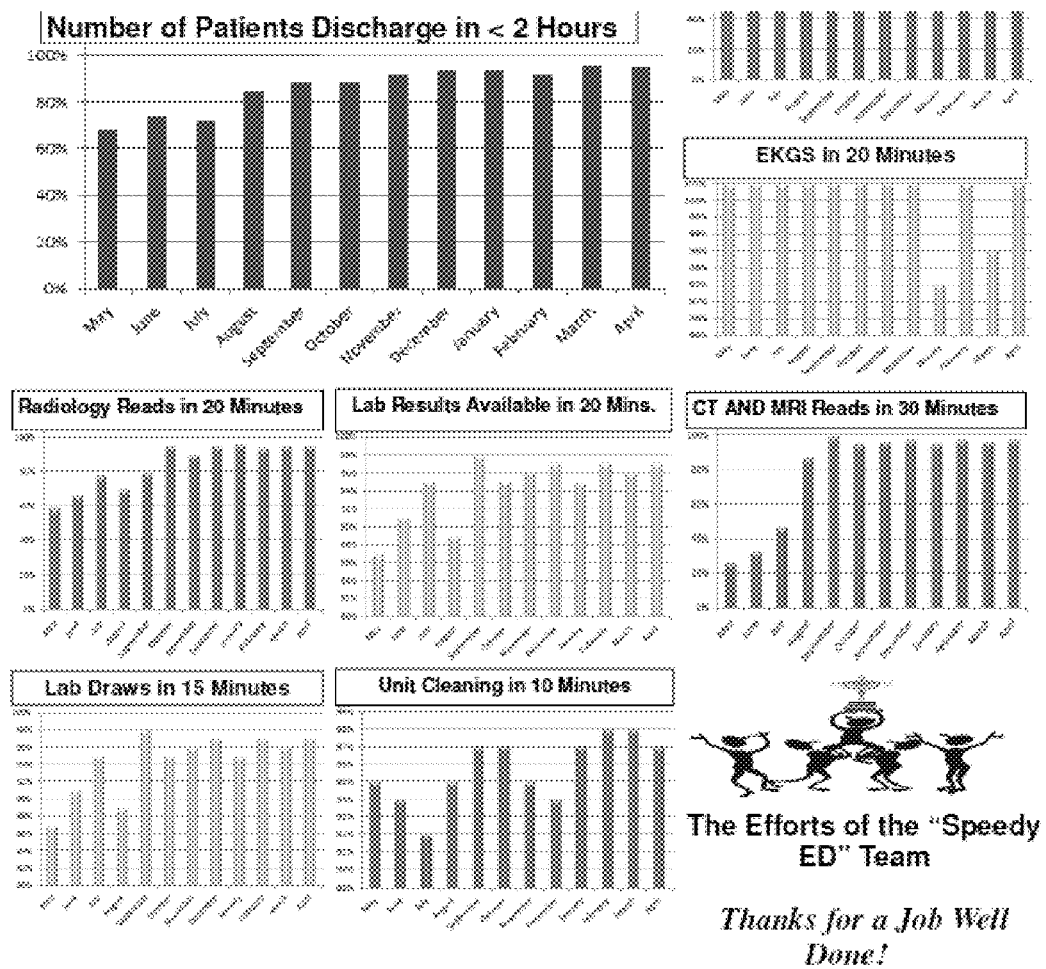
FIG. 34 is a screenshot of part two of a graphical scorecard to track the progress of performance improvement initiatives.

To convert a performance improvement calendar into an at-a-glance graphic, simply click "Show Report", as seen in the screenshot of FIG. 32. Graphical reports provide an easy to use visual representation of status and progress. Graphical report formats tends to be highly effective in helping to foster healthy performance improvement initiatives. First, it makes it easy to absorb a lot of information in a short period of time as it play to the adage that a picture paints a thousand words. It would require a several page report to convey the same information in a narrative report that can be communicated in a one page report. It also reduces a lot of the subjectivity that is common in a narrative report. The Strategic Quality Support System further comprises a process performance output stored on computer readable media and displayed on a computer monitor where improvements to existing systems are depicted for a specific historical period. The process performance output can be seen in FIGS. 33 and 34, and allows all contributing Departments and professional groups to visualize the impact of their contributions on the large goals and on one another. It fosters a team-based approach that is frequently difficult to achieve in many other approaches. It allows everyone to appreciate one another's contributions and to know who is holding the initiative back.

Figure 35:
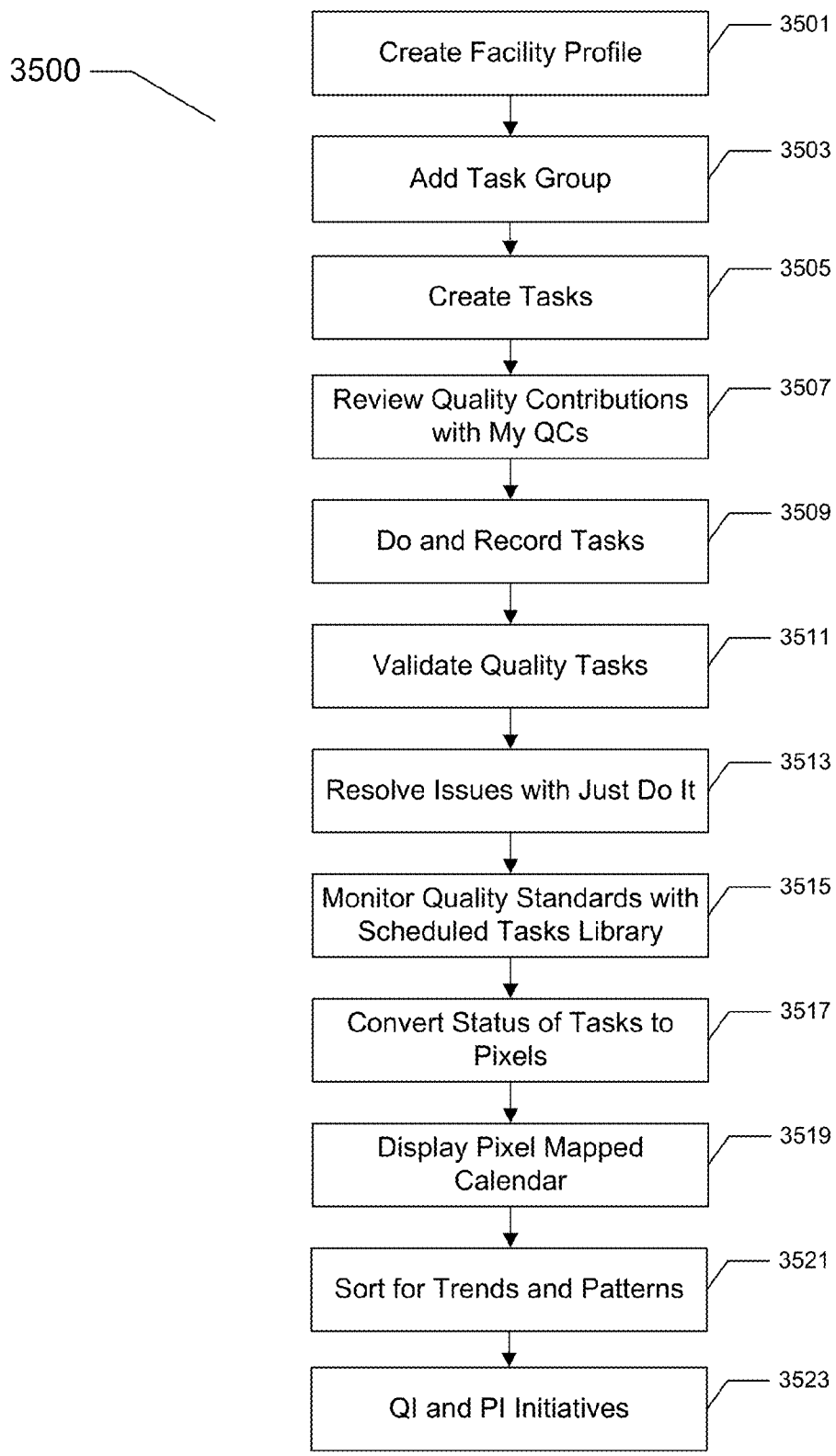
FIG. 35 is a flowchart depicting a method of the present invention.

Turning lastly to FIG. 35, a method of the present invention is depicted. A method for strengthening a healthcare provider's quality program 3500 can be seen in FIG. 35. A facility profile is created in a computer program in step 3501. The facility profile contains the hierarchy and structure of the facility such as departments, users, committees, and the like. The facility profile may be created manually or using an electronic source such as a spreadsheet, database, or the like. Task groups are then added in step 3503. Adding a task group allows for multiple users to be assigned to a task or a set of tasks. Tasks are then created in step 3505 in a computer program. Tasks are created using either a task template or a task wizard. The task is described, scheduled, and assigned. In step 3507, a user's quality contributions can be reviewed using the My QCs function. This step provides a list of currently scheduled tasks and allows a user to easily document the status of their responsibilities. Tasks are then performed and recorded in step 3509. Quality tasks are validated in step 3511. The Strategic Quality Support System will schedule validation reviews of quality activities. Issues can be immediately resolved using a Just Do It function in step 3513. This function allows for fixing something where the immediate fix resolves the issue, and provides for a means of reporting these types of activities. In step 3515, quality standards are monitored with a scheduled tasks library where all current standards being monitored within an organization are contained. In step 3517, the status of a quality task for a given date is converted to a pixel that provides a color representation of the status of a specified quality task. In step 3519, these pixels are aggregated into a pixel mapped calendar that is displayed on a computer screen or the like. The pixels may further contain sub-pixels, lack of color, cross-hatching, or the like to convey important quality information about each task. In step 3521, the pixels may be sorted by status to look for trends and patterns. Finally, in step 3523 Quality Improvement (QI) and Performance Improvement (PI) Initiatives are undertaken to strengthen systems important to patient safety.

The integration of the Quality Assurance (QA) module, the Quality Improvement (QI) module, and the Performance Improvement (PI) module therefore provides a Strategic Quality Support System (SQSS) that strengthens a healthcare provider's quality programs and operations.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims, and the attached drawings.

What is claimed is:

1. A computer-based Strategic Quality Support System for strengthening a healthcare provider's quality program comprising:
   a computer having a processor, memory, and access to computer readable media;
   a computer program stored on computer readable media having a quality assurance module, a quality improvement module, and a performance improvement to module;
   a user interface displayed on a computer monitor for interaction with said computer program;
   a network connection between the computer and a computer network for allowing remote access to the computer program;
   a pixel mapped calendar stored on computer readable media and graphically displayed on a computer monitor having a plurality of colored geometries arranged in rows and columns for each date, each colored geometry representing status of a quality assurance task and being assigned a color corresponding to a current status of a quality assurance task;
   whereas the arrangement and clustering of like colored geometries in the pixel mapped calendar provides for real time pattern recognition of trends and weaknesses in a healthcare providers systems through the overall view of the plurality of colored geometries in each date;
   a task overview function stored on computer readable media and displayed on a computer monitor containing a visual representation of task compliance for each quality assurance task using a plurality of colored geometries where each color has significance; and
   a task compliance output stored on computer readable media and displayed on a computer monitor where quality assurance compliance percentages are depicted for a specified historical period.

2. The system of claim 1, further comprising a facility profile creation function stored on computer readable media.

3. The system of claim 1, further comprising a My QC's function stored on computer readable media for providing a user with their quality contributions.

4. The system of claim 1, further comprising a validation function stored on computer readable media for validating quality tasks.

5. The system of claim 1, further comprising a task group addition function stored on computer readable media for allowing multiple users to be assigned to a task.

6. The system of claim 1, further comprising a Just Do It function stored on computer readable media for immediate resolution of an issue.

7. The system of claim 1, further comprising a task creation function stored on computer readable media for describing, scheduling, and assigning a task.

8. The system of claim 1, further comprising a scheduled tasks library stored on computer readable media that contains current standards being monitored.

9. The system of claim 1, further comprising a manage absences function stored on computer readable media for moving tasks from one person to another.

10. The system of claim 1, further comprising as process performance output stored on computer readable media and displayed on a computer monitor where improvements to existing systems are depicted for a specific historical period.

11. A pixel mapped calendar stored on computer readable media and graphically displayed on a computer monitor comprising a plurality of colored geometries arranged in rows and columns for each date, each colored geometry representing status of a quality assurance task and being assigned a color corresponding to a current status of a quality assurance;
   whereas the arrangement and clustering of like colored geometries in the pixel mapped calendar provides for real time pattern recognition of trends and weaknesses in operational systems through the overall view of the plurality of colored geometries in each date.

12. The pixel mapped calendar of claim 11, wherein the colored geometries further comprise overlays arranged around the colored geometries whereas the overlays are of a different color than the colored geometries to provide further information regarding current status of a quality assurance task.

13. The pixel mapped calendar of claim 12, wherein overlays comprise more than one geometric shape.

14. The pixel mapped calendar of claim 12, wherein the overlays are arranged around the colored geometries such that a secondary color appears as a border around a primary color of the colored geometry.

15. The pixel mapped calendar of claim 11, wherein at least some of the displayed colored geometries have no color content.

16. The pixel mapped calendar of claim 11, wherein at least some of the displayed colored geometries have a cross hatching.

17. The pixel mapped calendar of claim 11, further comprising a filter for sorting by status.

18. A method for strengthening a healthcare provider's quality program, the method comprising the steps of:
   creating a facility profile on as computer having a processor, memory and computer readable media;

adding a task group on the computer:
creating tasks on the computer;
reviewing quality contributions with a my QC's function on the computer;
performing and recording tasks on the computer readable media;
validating on the computer quality tasks stored on the computer readable media;
resolving issues using a Just Do It-function on the computer;
monitoring quality standards using a scheduled tasks library stored on the computer readable media;
converting on the computer status of tasks recorded into colored geometries;
arranging the colored geometries into rows and columns for each date and displaying the arranged colored geometries on a computer screen;
sorting the colored geometries on the computer for trends and patterns;
whereas the arrangement and clustering of like colored geometries in the pixel mapped calendar provides for real time pattern recognition of trends and weaknesses in operational systems through the overall view of the plurality of colored geometries in each date; and
engaging in quality and performance improvement initiatives.

19. The method of claim 18, wherein at least some of the colored geometries have an overlay of a different color than he colored geometries to provide further information regarding current status of a quality assurance task.

20. The method of claim 19, wherein the overlays are arranged near a colored geometry such that a secondary color appears as a border around a primary color of the colored geometry.

21. The method of claim 19, wherein at least some of the displayed colored geometries have a cross hatching.

* * * * *